(12) United States Patent
Okamoto et al.

(10) Patent No.: US 6,297,008 B1
(45) Date of Patent: Oct. 2, 2001

(54) PROCESS FOR DETECTING TARGET NUCLEIC ACID, PROCESS FOR QUANTIFYING THE SAME, AND PYRYLIUM COMPOUND FOR CHEMILUMINESCENCE ANALYSIS

(75) Inventors: Tadashi Okamoto, Yokohama; Nobuko Yamamoto, Isehara, both of (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 08/943,019

(22) Filed: Oct. 2, 1997

(30) Foreign Application Priority Data

Oct. 3, 1996 (JP) .................................................. 8-262818
Oct. 3, 1996 (JP) .................................................. 8-262819
Oct. 3, 1996 (JP) .................................................. 8-262820

(51) Int. Cl.[7] ............................................................ C12Q 1/68
(52) U.S. Cl. ............................... 435/6; 436/501; 536/25.3
(58) Field of Search ......................... 435/6, 810; 436/501; 536/25.3; 935/77.78

(56) References Cited

U.S. PATENT DOCUMENTS

| 3,786,369 | 1/1974 | Drexhage et al. | 331/94.5 |
|---|---|---|---|
| 4,341,894 | 7/1982 | Regan et al. | 544/333 |

(List continued on next page.)

FOREIGN PATENT DOCUMENTS

| 0229943 | 7/1987 | (EP) . | |
|---|---|---|---|
| 0232967 | 8/1987 | (EP) . | |
| 0294921 | 12/1988 | (EP) | A61K/31/44 |
| 0315491 | 5/1989 | (EP) . | |
| 0320308 | 6/1989 | (EP) | C12Q/1/68 |
| 0367449 | 5/1990 | (EP) | C09B/23/02 |
| 0439036 | 7/1991 | (EP) . | |
| 0455517 | 11/1991 | (EP) | C12Q/1/68 |
| 0487218 | 5/1992 | (EP) . | |
| 0512334 | 11/1992 | (EP) . | |
| 0603783 | 6/1994 | (EP) | G01N/33/52 |
| 0643140 | 3/1995 | (EP) . | |
| 59-133460 | 7/1984 | (JP) . | |
| 64-52715 | 2/1989 | (JP) | A61K/31/44 |
| 1-153683 | 6/1989 | (JP) | C07D/309/34 |
| 1275528 | 11/1989 | (JP) | A61K/31/40 |
| 2-75958 | 3/1990 | (JP) . | |
| 2-295496 | 12/1990 | (JP) . | |
| 5-237000 | 9/1993 | (JP) . | |
| WO86-03227 | 6/1986 | (WO) . | |
| WO86-06374 | 11/1986 | (WO) . | |
| WO89-10415 | 11/1989 | (WO) . | |
| WO 93-15221 | 8/1993 | (WO) . | |

OTHER PUBLICATIONS

Balaban, et al; Pyrylium Salts Synthesis, Reactions, and Physical Properties; Suppl. 2, Advances in Heterocyclic Chemistry, pp. 173–219, (1977).

(List continued on next page.)

*Primary Examiner*—Ardin H. Marschel
(74) *Attorney, Agent, or Firm*—Fitzpatrick, Cella, Harper & Scinto

(57) ABSTRACT

The present invention provides a process for detecting or quantifying a target nucleic acid in a sample, the process comprising the steps of associating a chemiluminescent compound, capable of being associated with a double-stranded nucleic acid, with a double-stranded nucleic acid including the target nucleic acid, and detecting or measuring chemiluminescence derived from the chemiluminescent compound associated with the double-stranded nucleic acid. According to the process, the target nucleic acid in the sample can be highly sensitively detected, or precisely quantified.

38 Claims, 10 Drawing Sheets

U.S. PATENT DOCUMENTS

| | | | |
|---|---|---|---|
| 4,555,396 | 11/1985 | Frank et al. | 424/3 |
| 4,774,250 | 9/1988 | Chen et al. | 514/336 |
| 4,794,073 | 12/1988 | Dattagupta et al. | 435/6 |
| 4,840,784 | 6/1989 | Frank et al. | 424/3 |
| 4,992,257 | 2/1991 | Bonnett et al. | 424/9 |
| 5,047,419 | 9/1991 | Detty et al. | 514/432 |
| 5,162,519 | 11/1992 | Bonnett et al. | 540/145 |
| 5,229,297 | 7/1993 | Schnipelsky et al. | 436/94 |
| 5,278,043 | 1/1994 | Bannworth et al. | 536/231 |
| 5,340,716 | 8/1994 | Ullman et al. | 435/6 |
| 5,545,521 | 8/1996 | Okamoto et al. | 435/5 |
| 5,591,578 | 1/1997 | Meade et al. | 435/6 |
| 5,624,798 | 4/1997 | Yamamoto et al. | 435/6 |
| 5,670,315 | 9/1997 | Yamamoto et al. | 435/6 |

OTHER PUBLICATIONS

Pirelahi, et al. "The effect of Electron Withdrawing Groups on the Stability of Thiabenzenes", J. Heterocyclic Chem., vol. 14, pp. 199–201 (1977).

Chem. Abstract, vol. 126, No. 9, Abst. No. 115288n (XP–002057794), 1997.

Nakatsuji, et al. Synthesis of Pyrylium Salts From Trisubstituted 1,4–Pentadiyn–3–Ols With $HClO_4$ Tetrahedron Ltrs, 25, 45, p5143–5145 (1984).

Shimidzu, et al., "Synthesis . . . properties", 19th Symp. on Nuc. Acids. Chem, pp. 97–98 (1992).

Wizinger, et al., Helv. Chim. Acta, vol. 39, No. 2, Fas. I, pp. 5–15 (1956).

Foerst, Newer Methods of Prep. Org. Chem., vol. II, Acad. Press pp. ix–xiv (1963).

Brun, et al., "Dynamics . . . Bases", J. Am. Chem. Soc., vol. 114, pp. 3656–3660 (1992).

Cardullo, et al., "Detection . . . transfer", Proc. Natl. Acad. vol. 85, pp. 8790–8794 (1988).

Rahman, et al., "Complexes . . . Cu (II)", Carcinogenesis, vol. II, No. 11, pp. 2001–2003 (1990).

Balaban, et al., "Charge–Transfer . . . Iodides", Tetrahedron, vol. 20, pp. 119–130 (1963).

Morrison, et al., "Solution . . . Hybridization", Anal. Biochem, vol. 183, pp. 231–244 (1989).

Basting, et al., "New Laser Dyes", Appl. Phys., vol. 3, pp. 81–88 (1974).

Latt, et al., "New . . . Acids", Cytometry, vol. 5, No. 4, pp. 339–347 (1984).

Murphy, et al., "Long–Range . . . Helix", Science, vol. 262, pp. 1025–1029 (1993).

Smits, et al., "Relationship . . . Dimethylsulfoxide", Anal. Chem. vol. 45, No. 2, pp. 339–342 (1973).

Fromherz, et al. "Photoinduced . . . methylviologen", JACS, vol. 108, pp. 5361–5362 (1986).

Ulicky, et al., Comp. Dict. of Phys Chem., p. 103 (1992).

Detty et al., "Chalcogenapyrylium . . . Oxidase", J. Med. Chem. vol. 33, pp. 1108–1116, (1990).

Balaban et al., "Regioselective . . . Groups", J. Labelled Cmpds and Radiopharm., vol. 19, No. 6, pp. 783–793 (1982).

Detty, "Rational . . . dyes", New Directions in Photodynamic Therapy, vol. 847, pp. 68–73 (1987).

Yamamoto, et al., "Novel . . . DNA," Nucleic Acids Sym. Series, No. 29, pp. 83–84 (1993).

Sanford, et al., "The Growth . . . Cells", J. Nat'l. Cancer Inst., vol. 9, No. 3, pp. 229–246 (1948).

Haucke, et al. "Absorption . . . Salts", Ber. Bunsonques. Phy. Chem. vol. 96, No. 7, pp. 880–886 (1992).

W. Foerst, New Methods of Preparative Organic Chemistry, Acad. Press. (1964).

W. Gregory Roberts, et al., "In Vitro Characterization of Monoaspartyl Chlorin $e_6$ and Diaspartyl Chlorin $e_6$ for Photodynamic Therapy," Journal of The National Cancer Institute, May 4, 1988, vol. 80, No. 5.

M.J. Manyak, et al., "Photodynamic Therapy," Journal of Clinical Oncology, vol. 6, No. 2, pp. 380–391 (Feb. 1988).

"PCR Protocols," ed. by Innis, et al., Academic Press (1990).

R. Wizinger, et al., Helvitica Chimica Acta, vol. 39, No. 24, pp. 217–222, (1956).

Yamamoto et al., Nucl. Acids Res, 23(8), pp. 1445–1446 (1995).

Picard, et al., Appl. Environ, Bicrobiol, 58(9), pp. 2717–2722 (1992).

Strobel, et al., "Preparation and Characterization . . . DNA Hybridization," Bioconjugate Chem., vol. 2, pp. 89–95 (1991).

Purugganan, et al., "Accelerated Electron . . . DNA," Science, vol. 241, No. 23, pp. 1645–1649 (1988).

Cullis, et al., "Electron Conduction and Trapping in DNA," J. Chem. Soc. Faraday Trans., vol. 86, No. 3, pp. 591–592 (1990).

Barton, et al., "DNA–Mediated Photoelectron Transfer Reactions." J. Am. Chem. Soc., vol. 108, pp. 6391–6393 (1986).

Halvorson, et al. "Means of Determining Bacterial Population by the Dilution Method," J. Bact., vol. 25, pp. 101–121 (1933).

Rye, et al., "Stable Fluorescent Examples of Double–Stranded DNA," Nucl. Acids, Res., vol. 20, No. 11, pp. 2803–2812 (1992).

Blasko, et al., "Approaches to the Synthesis of Benzo[c] Phenanthridines," J. Heterocycl. Chem., vol. 26, No. 6, pp. 1601–1603, Abstract Only (1989).

Chatterjea, et al., "Synthesis of 2–phenyl[1,2–b]naphthopyrylium salts: a study of Michael reactions with 1–naphthol," Natl. Acad. Sci. Lett. (India), 11(10), pp. 311–312, Abstract Only (1988).

Tilak, et al., "Synthesis of Sulfur Heterocyclics Part X: Mono–& Diacationoid Heterocyclic Systems Containing One & Two Sulfur Atoms," Indian J. Chem., 7(10), pp. 948–951, Abstract Only (1969).

Bringman, et al., "Novel Concepts in Directed Biaryl Synthesis XXXVIII, Synthesis and Structure of a Protected Lactolate–Bridged Biaryl with Relevance to the Atropisomer–Selective Ring Opening of Biaryl Lactones," Liebigs Ann. Chem., No. 4, pp. 439–444, Abstract Only (1994).

PROCESS FOR DETECTING TARGET NUCLEIC ACID, PROCESS FOR QUANTIFYING THE SAME, AND PYRYLIUM COMPOUND FOR CHEMILUMINESCENCE ANALYSIS

BACKGROUND OF THE INVENTION

1. Field of the Invention

The present invention relates to a chemiluminescence-utilizing process for detecting or quantifying a target nucleic acid, and a pyrylium compound used for chemiluminescence analysis.

2. Description of the Related Art

Nowadays, detection of double-stranded nucleic acids or specific genes, i.e. single-stranded nucleic acids having specific base sequences, is routinely carried out in various fields such as medicine, criminal investigations, and agriculture (hereinafter, such double- or single-stranded nucleic acids are referred to as target nucleic acids).

Double-stranded nucleic acids in samples have been detected, for example, as follows: A double-stranded nucleic acid is separated by electrophoresis using a polyacrylamide gel or an agarose gel; the resultant is then stained with a fluorochrome which can be intercalated between adjacent base pairs in the double-stranded nucleic acid to exhibit enhancement of fluorescence, such as ethidium.bromide (EB); the fluorochrome intercalated into the double-stranded nucleic acid is excited by a transilluminator with an ultraviolet lamp; and the fluorescence emitted from the fluorochrome is detected.

Similarly, a double-stranded nucleic acid in a solution can be detected by staining the double-stranded nucleic acid with a fluorochrome such as EB, diamidinodiphenylindole dihydrochloride (DAPI) or Hoechst 33258, and detecting fluorescence emitted from the fluorochrome.

A problem with the detection of a double-stranded nucleic acid in a solution using an ordinary fluorochrome whose fluorescence is enhanced by being associated with the double-stranded nucleic acid is low detection sensitivity in many cases. Fluorescence detection itself is more sensitive than more conventional colorimetry. The absolute sensitivity-limit of fluorescence detection, however, falls within a magnitude in the order of a few nM due to problems inherent in fluorescence measurement, such as leaking light derived from excitation light, and Raman scattering light from the solvent molecules when the sample is liquid. In particular, the sensitivity of fluorescence detection is not satisfactory for directly detecting a trace-amount or low-concentration of double-stranded nucleic acid derived from an organism.

Further, another problem with the detection of a double-stranded nucleic acid using a fluorochrome is the rise of the background during the detecting step due to fluorescence emission from the free fluorochrome molecules not associated with the double-nucleic acid when irradiated with ultraviolet rays. Such raised background can be a cause of lowered detection sensitivity.

As a remedy to solve the problem concerning the rise of the background, Japanese Patent Laid-Open No. 7-174759 (corresponding to U.S. Pat. No. 5,624,798) discloses a method using a pyrylium compound which has a specific structure and exhibits fluorescence only when it is associated with a double-stranded nucleic acid. According to this method, the detection sensitivity has been markedly improved, and detection utilizing fluorescence has markedly become practicable.

Although the detection sensitivity has been improved by reducing the level of the background, the above-described problems inherent in detection utilizing fluorescence, such as leakage of light and generation of Raman scattering light, has not yet been sufficiently solved. Accordingly, there has been a demand for a method to further improve the detection sensitivity.

Meanwhile, single-stranded nucleic acids having specific base sequences have been detected, for example, by a so-called probe method using a labelled nucleic acid as a probe. Various probe methods have been developed, in which radioisotopes, bioluminescent techniques or chemiluminescent techniques are employed to achieve high sensitivity.

In probe methods using radioisotopes, labels containing radio active atoms (radioisotopes) are used, and the detection sensitivity is satisfactory, and theoretically even one molecule (one copy) of the target nucleic acid can be detected. Such probe methods using radioisotopes, however, require special facilities, and the operation is accompanied by dangers. Further, since radioisotopes are unstable, probe nucleic acids labelled with radioisotopes cannot be stably stored for long time periods.

In contrast, probe methods using conventional chemical staining methods or enzymatic staining methods are more practical since they do not require special facilities, and the operation is relatively safe. Such probe methods using conventional staining methods are, however, markedly inferior in sensitivity to those using radioisotopes, and cannot sufficiently cope with detection of nucleic acids which can be obtained only in extremely small quantities, such as nucleic acids derived from organismal samples. Further, in many cases, probe nucleic acids bonded with labelling substances for such conventional staining methods are also unstable, and cannot be stored for long time periods.

SUMMARY OF THE INVENTION

An object of the present invention is to provide a sensitized process for detecting a target single-stranded nucleic acid in a sample.

Another object of the present invention is to provide a process for more precisely quantifying a target single-stranded nucleic acid in a sample.

Further, another object of the present invention is to provide a process for more sensitively detecting a target double-stranded nucleic acid in a sample.

Further object of the present invention is to provide a more precise process for quantifying a target double-stranded nucleic acid in a sample.

Moreover, another object of the present invention is to provide a highly sensitive process for detecting a single-stranded nucleic acid in a sample without complicated procedures.

Furthermore, another object of the present invention is to provide a process for highly precisely quantifying a target single-stranded nucleic acid in a sample without complicated procedures.

Furthermore, another object of the present invention is to provide a highly sensitive process for detecting a double-stranded nucleic acid in a sample with a simple procedure.

Moreover, another object of the present invention is to provide a process for highly precisely quantifying a target double-stranded nucleic acid in a sample.

Still further, another object of the present invention is to provide a compound for use in a chemiluminescence analysis.

According to an aspect of the present invention, there is provided a process for detecting a target single-stranded nucleic acid having a first base sequence comprising the steps of:
   forming a double-stranded nucleic acid by hybridizing the target single-stranded nucleic acid with a probe nucleic acid having a second base sequence complementary to the first base sequence;
   providing a chemiluminescent compound capable of being associated with a double-stranded nucleic acid, and then associating the chemiluminescent compound with the double-stranded nucleic acid resulting from the above forming step; and
   detecting luminescence from the chemiluminescent compound associated with the double-stranded nucleic acid.

According to another aspect of the present invention, there is provided a process for quantifying a target single-stranded nucleic acid having a first base sequence comprising the steps of:
   forming a double-stranded nucleic acid by hybridizing the target single-stranded nucleic acid with a probe nucleic acid having a second base sequence complementary to the first base sequence;
   providing a chemiluminescent compound capable of being associated with a double-stranded nucleic acid, and then associating the chemiluminescent compound with the double-stranded nucleic acid resulting from the above forming step; and
   measuring luminescence from the chemiluminescent compound associated with the double-stranded nucleic acid.

According to these aspects, since the sensitivity of the detection of the target nucleic acid is quite high, it is not necessary to employ a target nucleic acid-amplifying process, such as PCR process. Further, since chemiluminescence is utilized for detecting or quantifying the double-stranded nucleic acid including the target nucleic acid, the above-described problems inherent in fluorescence methods can be removed.

Moreover, since the chemiluminescent compound may be added after hybridization and does not necessarily have to be previously linked to the probe nucleic acid, the probe nucleic acid can be prevented from being destabilized, which may occur in the case where the probe nucleic acid is labelled.

The detection of the double-stranded nucleic acid including the target nucleic acid is carried out in a state where the chemiluminescent compound is associated with the double-stranded nucleic acid, or under a condition in which the chemiluminescent compound acquires chemiluminescent ability only when associated with double-stranded nucleic acids. According to such a manner, since the step of removing the chemiluminescent compound molecules not associated with the double-stranded nucleic acid from the reaction system becomes unnecessary, the detecting operation can be simplified, and a highly sensitive detection on an effectively lowered background can be achieved.

Further, according to another aspect of the present invention, there is provided a process for detecting a target double-stranded nucleic acid comprises the steps of:
   providing a chemiluminescent compound capable of being associated with a double-stranded nucleic acid, and then associating the chemiluminescent compound with the target double-stranded nucleic acid; and
   detecting luminescence from the chemiluminescent compound associated with the target double-stranded nucleic acid.

Meanwhile, according to another aspect of the present invention, there is provided a process for quantifying a target double-stranded nucleic acid comprises the steps of:
   providing a chemiluminescent compound capable of being associated with a double-stranded nucleic acid, and then associating the chemiluminescent compound with the target double-stranded nucleic acid; and
   measuring luminescence from the chemiluminescent compound associated with the target double-stranded nucleic acid.

According to these aspects, the problems inherent in detecting methods using fluorochromes, such as leaking light derived from excitation light and Raman scattering, are removed, and double-stranded nucleic acids can be highly sensitively detected. These aspects in combination with, for example, a photo-counting technique, provide a possibility of one-molecule-level detection of the chemiluminescent compound associated with a target double-stranded nucleic acid. That is, the sensitivity of the detection of a double-stranded nucleic acid can be further markedly improved as compared to fluorescence detecting process.

In these aspects, it is preferable that the luminescence-detecting step is carried out under a condition in which only the chemiluminescent compound molecules associated with the double-stranded nucleic acid can exhibit chemiluminescence, or the chemiluminescent compound is selected from compounds which acquire chemiluminescent ability only when associated with double-stranded nucleic acids. According to this manner, even if the chemiluminescent compound not associated with the double-stranded nucleic acid coexists with the target nucleic acid, the background level for detecting luminescence is not raised, and the target double-stranded nucleic acid can be detected or quantified at an extremely high sensitivity, such as a concentration level of 0.1 fM (in terms of base pair) or an absolute-quantity level of 0.1 attomoles (in terms of base pair).

In the above-described embodiments, for example, the structure of the chemiluminescent compound is changed through the association with the double-stranded nucleic acid, such as contact or binding reaction, with the double-stranded nucleic acid, and as a result, the chemiluminescent compound finally becomes luminescence-emissive. Typical examples of such an association include groove-binding, and intercalation in which the chemiluminescent compound is inserted between oligonucleotides of the double-stranded nucleic acid.

In such a case, the chemiluminescent compound becomes luminescence-emissive only when being associated with a double-stranded nucleic acid, and the compound which is not associated with a double nucleic acid does not emit chemiluminescence. Due to such a mechanism, when detecting the luminescence, the influence of the background level can be removed, and therefore, the detection for the target nucleic acid can be carried out highly sensitively.

Furthermore, according to another aspect of the present invention, there is provided a process for detecting a target single-stranded nucleic acid having a first base sequence comprising the steps of:
   forming a double-stranded nucleic acid by hybridizing the target nucleic acid with a probe nucleic acid having a second base sequence complementary to the first base sequence;
   providing a compound capable of being intercalated into a double-stranded nucleic acid and exhibiting chemiluminescence only in a hydrophobic environment, and then intercalating the compound into the double-stranded nucleic acid resulting from the above forming step; and placing in an aqueous medium the double-stranded nucleic acid into which the compound is intercalated together with a reagent capable of causing said compound to exhibit chemiluminescence, and then detecting the resulting chemiluminescence.

Moreover, according to another aspect of the present invention, there is provided a process for quantifying a target single-stranded nucleic acid having a first base sequence comprising the steps of:

forming a double-stranded nucleic acid by hybridizing the target nucleic acid with a probe nucleic acid having a second base sequence complementary to the first base sequence;

providing a compound capable of being intercalated into a double-stranded nucleic acid and exhibiting chemiluminescence only in a hydrophobic environment, and then intercalating the compound into the double-stranded nucleic acid resulting from the above forming step; and placing in an aqueous medium said double-stranded nucleic acid into which said compound is intercalated together with a reagent capable of causing said compound to exhibit chemiluminescence, and then measuring the resulting chemiluminescence.

Further, according to another aspect of the present invention, there is provided a process for detecting a target double-stranded nucleic acid comprising the steps of:

providing a compound capable of being intercalated into a double-stranded nucleic acid and exhibiting chemiluminescence only in a hydrophobic environment, and then intercalating the compound into the target double-stranded nucleic acid; and placing in an aqueous medium said double-stranded nucleic acid into which said compound is intercalated together with a reagent capable of causing said compound to exhibit chemiluminescence, and detecting the resulting chemiluminescence.

Still further, according to another aspect of the present invention, there is provided a process for quantifying a target double-stranded nucleic acid comprising the steps of:

providing a compound capable of being intercalated into a double-stranded nucleic acid and exhibiting chemiluminescence only in a hydrophobic environment, and then intercalating the compound into the target double-stranded nucleic acid; and placing in an aqueous medium said double-stranded nucleic acid into which said compound is intercalated together with a reagent capable of causing said compound to exhibit chemiluminescence, and then measuring the resulting chemiluminescence.

According to these aspects, only the chemiluminescent compound captured as an intercalator in the double-stranded nucleic acid can acquire an ability to emit luminescence. In other words, free molecules of the chemiluminescent compound, which is not intercalated into the double-stranded nucleic acid, do not raise the background level of the detecting or quantifying system when the target nucleic acid should be detected or quantified. Accordingly, even if the double-stranded nucleic acid containing the intercalator chemiluminescent compound coexists with free molecules of the chemiluminescent compound, the target nucleic acid can be highly sensitively detected and precisely quantified.

Furthermore, according to another aspect of the present invention, there is provided a chemiluminescent compound represented by the following general formula [1] for use in chemiluminescence analysis.

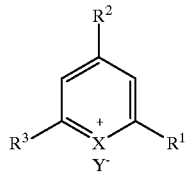

[1]

In the above formula:

X is O, S, Se or Te;

two of $R^1$, $R^2$ and $R^3$ are independently a substituted or unsubstituted aryl group;

the other is a hydrogen atom, halogen atom, sulfonate group, amino group, styryl group, nitro group, hydroxyl group, carboxyl group, cyano group, substituted or unsubstituted alkyl group, substituted or unsubstituted cycloalkyl group, —A or —L—A, wherein:

L is —$L^1$—, —$L^2$—$L^3$— or —$L^4$—$L^5$—$L^6$—, wherein each of $L^1$ to $L^6$ is independently —(CH=CH)—, a divalent group derived from the substituted or unsubstituted aryl group, a substituted or unsubstituted lower alkylene group, or —CH=$R^4$—, wherein $R^4$ is a ring structure having an oxo group; and A is a substituted or unsubstituted aryl group, or —CH=$R^5$, wherein $R^5$ is a substituted or unsubstituted heterocyclic ring, substituted or unsubstituted cycloalkyl group or substituted or unsubstituted aromatic ring; and $Y^-$ is an anion.

The pyrylium salt compound represented by the above general formula [1] exhibits high luminescent intensities when being made to emit chemiluminescence. Further, such a pyrylium compound is capable of exhibiting chemiluminescence only when being intercalated into double-stranded nucleic acids, and therefore, the compound is extremely useful for detection of double-stranded nucleic acids.

These and other objects, features and advantages of the present invention will become more apparent upon a consideration of the following description of a number of embodiments of the present invention which will be described by way of example only with reference to the accompanying drawings.

DESCRIPTION OF THE PREFERRED EMBODIMENT

Figure 1:
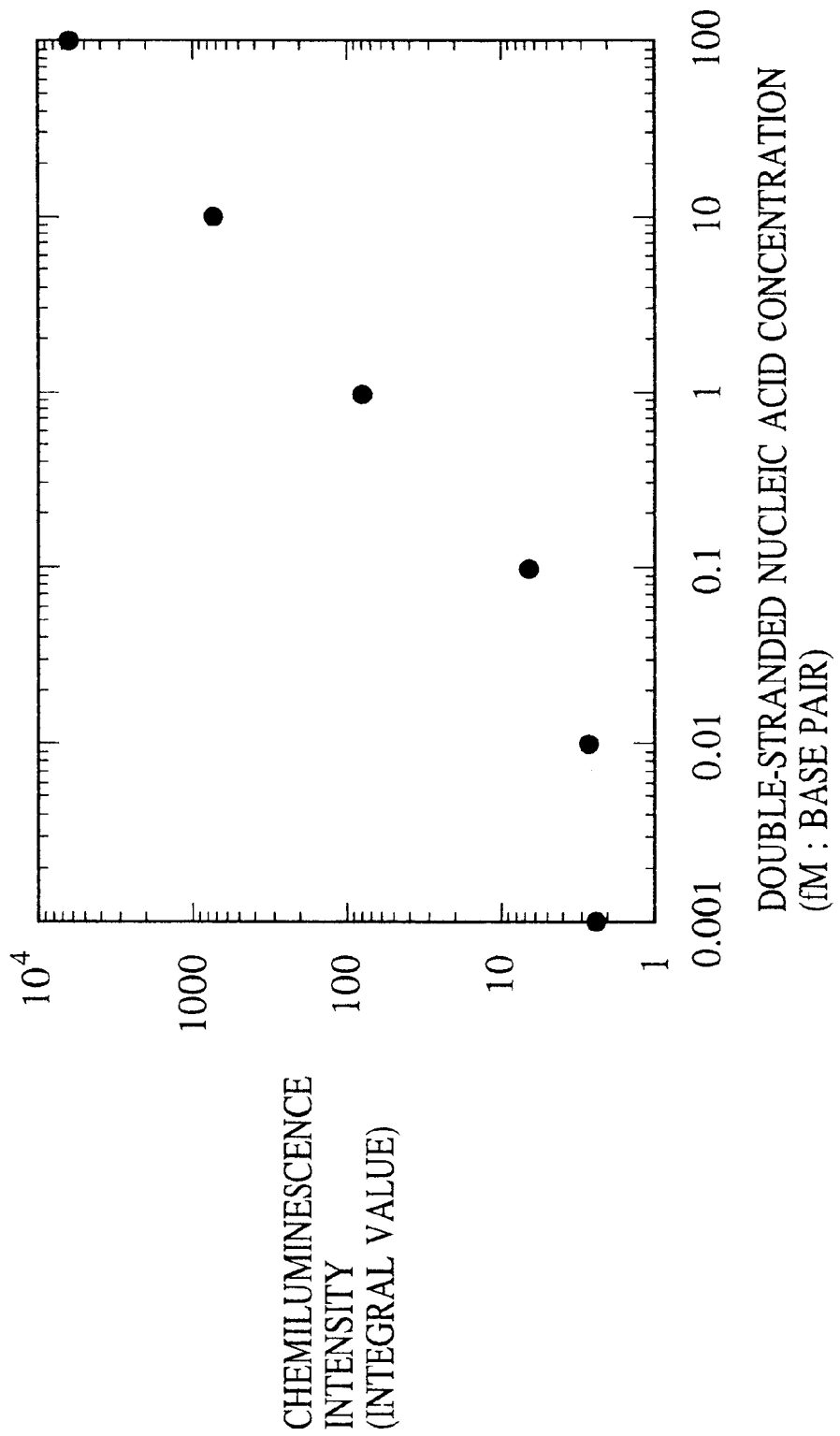
FIGS. 1, 2, 3, 4, 5, 6, 7, 8, 9, 10, 11 and 12 show the results of measurement of chemiluminescent intensity in Examples 2, 3, 4, 5, 6, 7, 8, 9, 10, 11, 13 and 14, respectively.

As employed herein the term "attomole" means $10^{-18}$ mole. The symbol "FM" is an abbreviation for femtomole or $10^{-15}$ mole.

Examples of nucleic acids to be subjected to detection or quantification of the embodiments according to the present invention, namely, examples of target nucleic acids, include various DNAs such as single- or double-stranded DNA and complementary DNA (cDNA) enzymically synthesized from messenger RNA (mRNA), and various RNA such as mRNA, transfer RNA (tRNA) and ribosomal RNA (rRNA). Incidentally, the sample subjected to analysis according to the present invention may include a plurality of different nucleic acids, and the present invention is suitably applicable to, for example, analysis of a total mRNA sample extracted from an living organism.

According to the present invention, since it is not necessary to bind a labelling substance to a probe nucleic acid, a modification of the probe nucleic acid's structure for labelling is not required. Therefore, the probe nucleic acid is free of limitation in view of labelling. As a probe nucleic acid, DNA, RNA and other modified nucleic acids having sequences necessary for desired hybridization can be used.

The chemiluminescent compound preferably possesses the properties of being stably held in a double-stranded nucleic acid when associated with the nucleic acid, and being able to generate sufficiently intense chemiluminescence in the associated state. Examples of association between the compound and the double-stranded nucleic acid include adsorption or binding of the compound to the double-stranded nucleic acid, incorporation of the compound into the double-stranded nucleic acid, and other various modes. In the present invention, preferred association modes are groove-binding, intercalation and the like in which the chemiluminescent compound is inserted into the double-stranded nucleic acid.

Examples of compounds capable of causing groove-binding and exhibiting luminescence when associated with a double-stranded nucleic acid include DAPI (4', 6-diamidino-2-phenylindole dihydrochloride; manufactured by, for example, Funakoshi Co., Ltd.) and YOYO-1 (manufactured by Molecular Probe Inc.).

In the case of using a chemiluminescent compound capable of being intercalated into the double helical structure of a double-stranded nucleic acid, namely, capable of serving as an intercalator, the environment surrounding the chemiluminescent compound changes as a result of intercalation. For example, when the chemiluminescent compound and the double-stranded nucleic acid are dissolved in an aqueous medium, the environment surrounding the compound changes to be more hydrophobic by intercalation. In addition, since the intercalated chemiluminescent compound is inserted between oligonucleotides of which the double-stranded nucleic acid consists, it is considered that the structure of the chemiluminescent compound changes when being intercalated. The degree of the structural change by intercalation is considered to be higher than that by other association modes such as groove-binding, and such structural change is preferred for the present invention. Further, when the chemiluminescent compound is capable of serving as an intercalator, only the intercalated molecules of the compound can be made to emit chemiluminescence based on the above-described environmental change and/or structural change.

Examples of chemiluminescent compounds having such properties of an intercalator include acridine orange, ethidium bromide, and pyrylium compound represented by the following general formula [1].

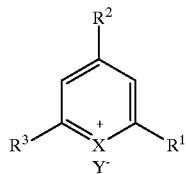

[1]

In the above formula:

X is O, S, Se or Te;

two of $R^1$, $R^2$ and R3 are independently a substituted or unsubstituted aryl group;

the other is a hydrogen atom, halogen atom, sulfonate group, amino group, styryl group, nitro group, hydroxyl group, carboxyl group, cyano group, substituted or unsubstituted alkyl group, substituted or unsubstituted cycloalkyl group, —A or —L—A, wherein:

L is —$L^1$—, —$L^2$—$L^3$— or —$L^4$—$L^5$—$L^6$—, wherein each of $L^1$ to $L^6$ is independently —(CH=CH)—, a divalent group derived from the substituted or unsubstituted aryl group, a substituted or unsubstituted lower alkylene group, or —CH=$R^4$—, wherein $R^4$ is a ring structure having an oxo group; and A is a substituted or unsubstituted aryl group, or —CH=$R^5$, wherein $R^5$ is a substituted or unsubstituted heterocyclic ring, substituted or unsubstituted cycloalkyl group, or substituted or unsubstituted aromatic ring; and $Y^-$ is an anion.

Examples of the substituted or unsubstituted aryl group include a phenyl group; aminophenyl group; dialkylaminophenyl group, such as a dimethylaminophenyl group and diethylaminophenyl group; carboxyphenyl group, azulenyl group (cyclopentacycloheptenyl group). These groups may have one or more substituents such as halogen atom and alkyl group. Further, in the case of the azulenyl group, such one or more substituents may also be dialkylaminophenyl groups such as a dimethylaminophenyl group and diethylaminophenyl group.

Examples of the alkyl group include a straight-chain or branched alkyl group having 1 to 6 carbon atoms, such as a methyl group, ethyl group, propyl group and butyl group. Examples of cycloalkyl group include a cyclopropyl group, cyclobutyl group, cyclopentyl group and cyclohexyl group. These groups may have one or more substituents such as halogen atoms and alkyl groups.

As to $L^1$ to $L^6$, examples of the divalent group derived from aryl group include an o-phenylene group, m-phenylene group and p-phenylene group, and these groups may have one or more substituents such as a halogen atom and alkyl group. Further, examples of the alkylene group include a straight-chain or branched lower alkylene group having 1 to 6 carbon atoms, such as a methylene group and ethylene group, and these groups may have one or more substituents such as a halogen atom and alkyl group.

As to the group A, example of the aryl group include the same aryl groups as those for the two substituents selected from $R^1$, $R^2$ and $R^3$.

As to the group $R^5$, examples of the heterocyclic ring include a furan ring, thiophene ring, pyrrole ring, pyran ring, thiopyran ring, pyridine ring and imidazole ring, and examples of substituent in such a heterocyclic ring include a halogen atom, straight-chain or branched alkyl group having 1 to 6 carbon atoms and dialkylaminophenyl group, such as a dimethylaminophenyl group and diethylaminophenyl group. Further, examples of the cycloalkyl group for the group $R^5$ include the same substituted or unsubstituted cycloalkyl group as that for one of $R^1$ to $R^3$. Moreover, examples of the aromatic ring for the group $R^5$ include a benzene ring, naphthalene ring and azulene ring, and examples of substituent in such an aromatic ring include a halogen atom, alkyl group and dialkylaminophenyl group, such as a dimethylaminophenyl group and diethylaminophenyl group.

Examples of the anion as $Y^-$ include $Cl^-$, $Br^-$, $I^-$, $ClO_4^-$, $SbF_6^-$, and $BF_4^-$. $I^-$ or $ClO_4^-$ is particularly preferably used.

Furthermore, more specific and preferred examples of the group —L— include the groups respectively represented by the following formulae [2] to [6].

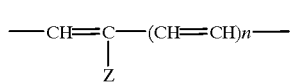

[2]

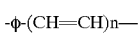

[3]

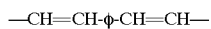

[4]

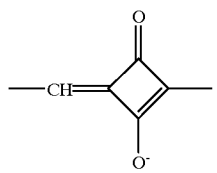

[5]

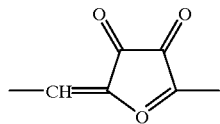

[6]

In the above formulae, Z is a hydrogen atom or a substituted or unsubstituted lower alkyl group, n is 0, 1 or 2, and φ is a substituted or unsubstituted o-, m- or p-phenylene group. Further, the lower alkyl group as the group Z in the above formula [2] may be, for example, a straight-chain or branched alkyl group having 1 to 6 carbon atoms, and an example of substituent which may be present in the alkyl group includes a halogen atom. Moreover, examples of substituent which may be present in the phenylene group φ in the above formula [3] or [4] include a halogen atom and alkyl group.

More specific and preferred examples of the compound represented by the general formula [1] include the pyrylium compounds respectively represented by the following general formulae [7] to [15].

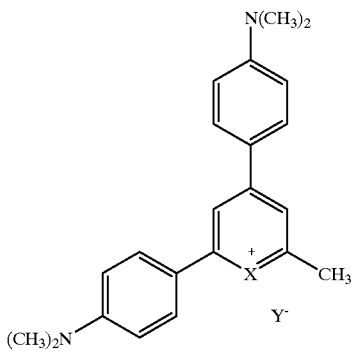

[7]

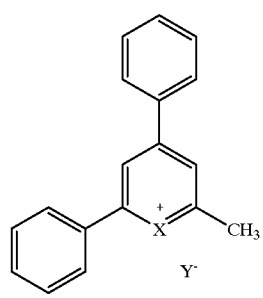

[8]

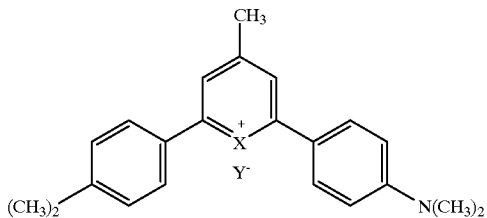

[9]

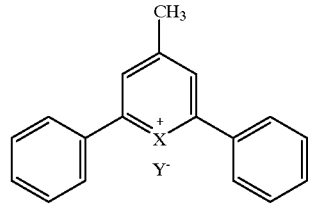

[10]

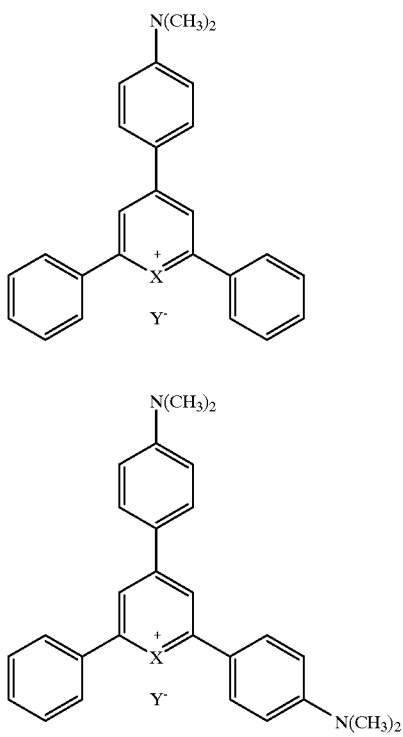

[11]

[12]

[13]

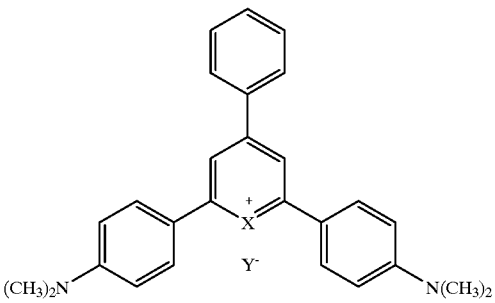

[14]

[15]

In the above formulae [7] to [15], X and Y are defined similarly to the general formula [1].

Further, still more specific examples of preferred pyrylium compound include the compounds listed in Table 1 which can be synthesized according to publicly-known processes, and the compounds which are based on the —$N(CH_3)_2$—containing compounds among the compounds listed in Table 1 and which have the group -H instead of the group —$N(CH_3)_2$. Compound 2 in Table 1 may be made by the prior art synthesis described in column 18, line 4 to column 19, line 19 and column 20, lines 1–5 of U.S. Pat. No. 5,624,798 issued Apr. 29, 1997, the aforesaid disclosure of which is herewith incorporated herein by reference.

TABLE 1

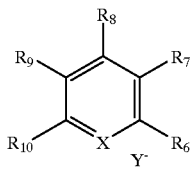

| Compound No. | X | Y | Ri | L | A |
|---|---|---|---|---|---|
| 1 | O | $ClO_4$ or I | $R_6 = CH_3$<br>$R_7 = H$<br>$R_8 = \phi\text{-}N(CH_3)_2$<br>$R_9 = H$<br>$R_{10} = A$ | | $\phi\text{-}N(CH_3)_2$ |
| 2 | S | $ClO_4$ or I | $R_6 = CH_3$<br>$R_7 = H$<br>$R_8 = \phi\text{-}N(CH_3)_2$ | | $\phi\text{-}N(CH_3)_2$ |

TABLE 1-continued

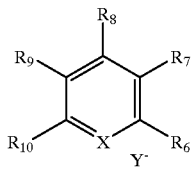

| Compound No. | X | Y | Ri | L | A |
|---|---|---|---|---|---|
| 3 | O | ClO$_4$ or I | R$_6$ = φ<br>R$_7$ = H<br>R$_8$ = A<br>R$_9$ = H<br>R$_{10}$ = A |  | φ-N(CH$_3$)$_2$ |
| 4 | S | ClO$_4$ or I | R$_6$ = φ<br>R$_7$ = H<br>R$_8$ = A<br>R$_9$ = H<br>R$_{10}$ = φ |  | φ-N(CH$_3$)$_2$ |
| 5 | O | ClO$_4$ or I | R$_6$ = φ<br>R$_7$ = H<br>R$_8$ = L-A<br>R$_9$ = H<br>R$_{10}$ = φ | General formula [2]<br>n = 0<br>Z = H | φ-N(CH$_2$CH$_3$)$_2$ |
| 6 | S | ClO$_4$ or I | R$_6$ = φ<br>R$_7$ = H<br>R$_8$ = L-A<br>R$_9$ = H<br>R$_{10}$ = φ | General formula [2]<br>n = 0<br>Z = H | φ-N(CH$_2$CH$_3$)$_2$ |
| 7 | O | ClO$_4$ or I | R$_6$ = φ<br>R$_7$ = H<br>R$_8$ = n = 0<br>R$_9$ = H<br>R$_{10}$ = L-A | General formula [2]<br>Z = H | φ-N(CH$_3$)$_2$ |
| 8 | S | ClO$_4$ or I | R$_6$ = φ<br>R$_7$ = H<br>R$_8$ = φ<br>R$_9$ = H<br>R$_{10}$ = L-A | General formula [2]<br>n = 0<br>Z = H | φ-N(CH$_3$)$_2$ |
| 9 | O | ClO$_4$ or I | R$_6$ = φ<br>R$_7$ = H<br>R$_8$ = L-A<br>R$_9$ = H<br>R$_{10}$ = φ | General formula [2]<br>n = 1<br>Z = H | φ-N(CH$_3$)$_2$ |
| 10 | S | ClO$_4$ or I | R$_6$ = φ<br>R$_7$ = H<br>R$_8$ = L-A<br>R$_9$ = H<br>R$_{10}$ = φ | General formula [2]<br>n = 1<br>Z = H | φ-N(CH$_3$)$_2$ |
| 11 | O | ClO$_4$ or I | R$_6$ = φ<br>R$_7$ = H<br>R8 = L-A<br>R$_9$ = H<br>R$_{10}$ = φ | General formula [2]<br>n = 1<br>Z = (—)CH=CH-φ-N(CH$_3$)$_2$ | φ-N(CH$_3$)$_2$ |
| 12 | S | ClO$_4$ or I | R$_6$ = φ<br>R$_7$ = H<br>R$_8$ = L-A<br>R$_9$ = H<br>R$_{10}$ = φ | General formula [2]<br>n = 1<br>Z = (—)CH=CH-φ-N(CH$_3$)$_2$ | φ-N(CH$_3$)$_2$ |
| 13 | O | ClO$_4$ or I | R$_6$ = φ<br>R$_7$ = H<br>R$_8$ = L-A<br>R$_9$ = H<br>R$_{10}$ = φ | General formula [3]<br>n = 1 | φ-N(CH$_3$)$_2$ |
| 14 | S | ClO$_4$ or I | R$_6$ = φ<br>R$_7$ = H<br>R$_8$ = L-A<br>R$_9$ = H<br>R$_{10}$ = φ | General formula [3]<br>n = 1 | φ-N(CH$_3$)$_2$ |
| 15 | O | ClO$_4$ or I | R$_6$ = φ<br>R$_7$ = H<br>R$_8$ = L-A | General formula [4] | φ-N(CH$_2$CH$_3$)$_2$ |

TABLE 1-continued

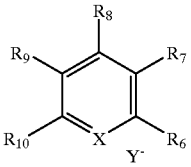

| Compound No. | X | Y | Ri | L | A |
|---|---|---|---|---|---|
| 16 | S | ClO₄ or I | R₆ = φ<br>R₇ = H<br>R₈ = L-A<br>R₉ = H<br>R₁₀ = φ | General formula [4] | φ-N(CH₂CH₃)₂ |
| 17 | O | ClO₄ or I | R₆ = φ<br>R₇ = H<br>R₈ = φ<br>R₉ = H<br>R₁₀ = L-A | General formula [4] | φ-N(CH₂CH₃)₂ |
| 18 | S | ClO₄ or I | R₆ = φ<br>R₇ = H<br>R₈ = φ<br>R₉ = H<br>R₁₀ = L-A | General formula [4] | φ-N(CH₂CH₃)₂ |
| 19 | O | ClO₄ or I | R₆ = φ<br>R₇ = H<br>R₈ = φ<br>R₉ = H<br>R₁₀ = L-A | General formula [5] | 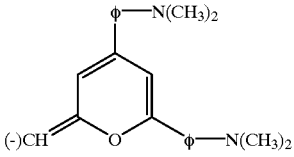 |
| 20 | S | ClO₄ or I | R₆ = φ<br>R₇ = H<br>R₈ = φ<br>R₉ = H<br>R₁₀ = L-A | General formula [5] | 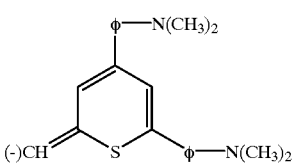 |
| 21 | O | ClO₄ or I | R₆ = φ<br>R₇ = H<br>R₈ = φ<br>R₉ = H<br>R₁₀ = L-A | General formula [5] | 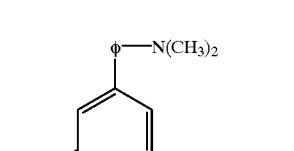 |
| 22 | O | ClO₄ or I | R₆ = φ<br>R₇ = H<br>R₈ = φ<br>R₉ = H<br>R₁₀ = L-A | General formula [6] | 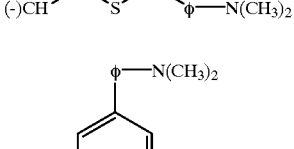 |
| 23 | S | ClO₄ or I | R₆ = φ<br>R₇ = H<br>R₈ = φ<br>R₉ = H<br>R₁₀ = L-A | General formula [6] | 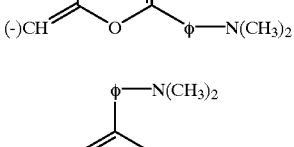 |

TABLE 1-continued

| Compound No. | X | Y | Ri | L | A |
|---|---|---|---|---|---|
| 24 | O | ClO₄ or I | R₆ = φ<br>R₇ = H<br>R₈ = φ<br>R₉ = H<br>R₁₀ = L-A | General formula [6] | |
| 25 | O | ClO₄ or I | R₆ = φ<br>R₇ = H<br>R₈ = φ<br>R₉ = H<br>R₁₀ = L-A | General formula [2]<br>n = O<br>Z = H | |
| 26 | S | ClO₄ or I | R₆ = φ<br>R₇ = H<br>R₈ = φ<br>R₉ = H<br>R₁₀ = L-A | General formula [2]<br>n = O<br>Z = H | |
| 27 | O | ClO₄ or I | R₆ = φ<br>R₇ = H<br>R₈ = φ<br>R₉ = H<br>R₁₀ = L-A | General formula [2]<br>n = O<br>Z = H | |
| 28 | S | ClO₄ or I | R₆ = φ<br>R₇ = H<br>R₈ = φ<br>R₉ = H<br>R₁₀ = L-A | General formula [2]<br>n = O<br>Z = H | |
| 29 | O | ClO₄ or I | R₆ = φ<br>R₇ = H<br>R₈ = φ<br>R₉ = H<br>R₁₀ = L-A | General formula [2]<br>n = O<br>Z = H | |
| 30 | O | ClO₄ or I | R₆ = φ<br>R₇ = H<br>R₈ = φ<br>R₉ = H<br>R₁₀ = L-A | General formula [2]<br>n = O<br>Z = H | |

TABLE 1-continued

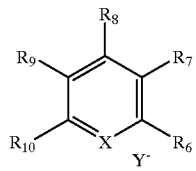

| Compound No. | X | Y | Ri | L | A |
|---|---|---|---|---|---|
| 31 | S | ClO₄ or I | R₆ = φ<br>R₇ = H<br>R₈ = L-A<br>R₉ = H<br>R₁₀ = φ | General formula [2]<br>n = O<br>Z = H | (-)CH=⟨pyran with S, φ-N(CH₃)₂ groups⟩ |
| 32 | O | ClO₄ or I | R₆ = φ<br>R₇ = H<br>R₈ = L-A<br>R₉ = H<br>R₁₀ = φ | General formula [2]<br>n = O<br>Z = H | (-)CH=⟨pyran with S, φ-N(CH₃)₂ groups⟩ |
| 33 | O or S | ClO₄ or I | R₆ = φ-N(CH₃)₂<br>R₇ = H<br>R₈ = A<br>R₉ = H<br>R₁₀ = φ-N(CH₃)₂ | | φ-N(CH₃)₂ |
| 34 | O or S | ClO₄ or I | R₆ = φN(CH₃)₂<br>R₇ = H<br>R₈ = A<br>R₉ = H<br>R₁₀ = φ-N(CH₃)₂ | | CH₃ |
| 35 | O or S | ClO₄ or I | R₆ = φ-N(CH₃)₂<br>R₇ = H<br>R₈ = A<br>R₉ = H<br>R₁₀ = φ-N(CH₃)₂ | | φ-COOH |
| 36 | O or S | ClO₄ or I | R₆ = φ-N(CH₃)₂<br>R₇ = H<br>R₈ = L-A<br>R₉ = H<br>R₁₀ = φ-N(CH₃)₂ | General formula [2]<br>n = O<br>Z = H | φ-N(CH₃)₂ |
| 37 | O or S | ClO₄ or I | R₆ = φ-N(CH₃)₂<br>R₇ = H<br>R₈ = L-A<br>R₉ = H<br>R₁₀ = φ-N(CH₃)₂ | General formula [2]<br>n = 1<br>Z = H | φ-N(CH₃)₂ |
| 38 | O or S | ClO₄ or I | R₆ = φ-N(CH₃)₂<br>R₇ = H<br>R₈ = L-A<br>R₉ = H<br>R₁₀ = φ-N(CH₃)₂ | General formula [3]<br>n = 1 | φ-N(CH₃)₂ |
| 39 | O or S | ClO₄ or I | R₆ = φ-N(CH₃)₂<br>R₇ = H<br>R₈ = L-A<br>R₉ = H<br>R₁₀ = φ-N(CH₃)₂ | General formula [4] | φ-N(CH₃)₂ |
| 40 | O or S | ClO₄ or I | R₆ = φ-N(CH₃)₂<br>R₇ = H<br>R₈ = L-A<br>R₉ = H<br>R₁₀ = φ-N(CH₃)₂ | General formula [2]<br>n = O<br>Z = H | φ-COOH |
| 41 | O or S | ClO₄ or I | R₆ = φ-N(CH₃)₂<br>R₇ = H<br>R₈ = L-A<br>R₉ = H<br>R₁₀ = φ-N(CH₃)₂ | General formula [2]<br>n = 1<br>Z = H | φ-COOH |
| 42 | O | ClO₄ | R₆ = φ-N(CH₃)₂ | General | φ-COOH |

TABLE 1-continued

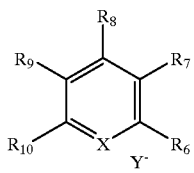

| Compound No. | X | Y | Ri | L | A |
|---|---|---|---|---|---|
| | or S | or I | $R_7$ = H<br>$R_8$ = L-A<br>$R_9$ = H<br>$R_{10}$ = φ-N(CH$_3$)$_2$ | formula [3]<br>n = 1 | |
| 43 | O<br>or S | ClO$_4$<br>or I | $R_6$ = 4)-N(CH$_3$)$_2$<br>$R_7$ = H<br>$R_8$ = L-A<br>$R_9$ = H<br>$R_{10}$ = φ-N(CH$_3$)$_2$ | General<br>formula [4] | φ-COOH |
| 44 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [2]<br>n = O<br>Z = H | φ-N(CH$_3$)$_2$ |
| 45 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [2]<br>n = 1<br>Z = H | φ-N(CH$_3$)$_2$ |
| 46 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [3]<br>n = 1 | φ-N(CH$_3$)$_2$ |
| 47 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [4] | φ-N(CH$_3$)$_2$ |
| 48 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [2]<br>n = O<br>Z = H | φ-COOH |
| 49 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [2]<br>n = 1<br>Z = H | φ-COOH |
| 50 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [3]<br>n = 1 | φ-COOH |
| 51 | O<br>or S | ClO$_4$<br>or I | $R_6$ = L-A<br>$R_7$ = H<br>$R_8$ = φ-N(CH$_3$)$_2$<br>$R_9$ = H<br>$R_{10}$ = φ-N(CH$_3$)$_2$ | General<br>formula [4] | φ-COOH |
| 52 | O<br>or S | ClO$_4$<br>or I | $R_6$ = A<br>$R_7$ = H<br>$R_8$ = φ-N(CH$_3$)$_2$<br>$R_9$ = H<br>$R_{10}$ = φ-N(CH$_3$)$_2$ | φ-COOH | |
| 53 | O<br>or S | ClO$_4$<br>or I | $R_6$ = A<br>$R_7$ = H<br>$R_8$ = φ-N(CH$_3$)$_2$<br>$R_9$ = H<br>$R_{10}$ = φ-N(CH$_3$)$_2$ | φ-COOH | |
| 54 | O<br>or S | ClO$_4$<br>or I | $R_6$ = φ<br>$R_7$ = H<br>$R_8$ = φ-N(CH$_3$)$_2$<br>$R_9$ = H<br>$R_{10}$ = φ-N(CH$_3$)$_2$ | | |
| 55 | O | ClO$_4$ | $R_6$ = φ-N(CH$_3$)$_2$ | | |

TABLE 1-continued

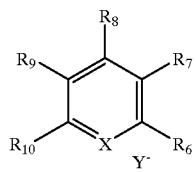

| Compound No. | X | Y | Ri | L | A |
|---|---|---|---|---|---|
| | or S | or I | $R_7$ = H<br>$R_8$ = φ<br>$R_9$ = H<br>$R_{10}$ = φ-N(CH$_3$)$_2$ | | |

Furthermore, especially preferred examples of pyrylium compounds include the following:
2-methyl-4,6-bis(4-N,N-dimethylaminophenyl)pyrylium iodide (general formula [7]: X=O and Y=I);
2-methyl-4,6-bis(4-N,N-dimethylaminophenyl)pyrylium perchlorate (general formula [7]: X=O and Y=ClO$_4$);
2-methyl-4,6-bis(4-N,N-dimethylaminophenyl)thiapyrylium iodide (general formula [7]: X=S and Y=I);
2-methyl-4,6-bis(4-N,N-dimethylaminophenyl)thiapyrylium perchlorate (general formula [7]: X=S and Y=ClO$_4$);
2-methyl-4,6-diphenylpyrylium iodide (general formula [8]: X=O and Y=I);
2-methyl-4,6-diphenylpyrylium perchlorate (general formula [8]: X=O and Y=ClO$_4$);
2-methyl-4,6-diphenylthiapyrylium iodide (general formula [8]: X=S and Y=I);
2-methyl-4,6-diphenylthiapyrylium perchlorate (general formula [8]: X=S and Y=ClO$_4$);
4-methyl-2,6-bis(4-N,N-dimethylaminophenyl)pyrylium iodide (general formula [9]: X=O and Y=I);
4-methyl-2,6-bis(4-N,N-dimethylaminophenyl)pyrylium perchlorate (general formula [9]: X=O and Y=ClO$_4$);
4-methyl-2,6-bis(4-N,N-dimethylaminophenyl)thiapyrylium iodide (general formula [9]: X=S and Y=I);
4-methyl-2,6-bis(4-N,N-dimethylaminophenyl)thiapyrylium perchlorate (general formula [9]: X=S and Y=ClO$_4$);
4-methyl-2,6-diphenylpyrylium iodide (general formula [10]: X=O and Y=I);
4-methyl-2,6-diphenylpyrylium perchlorate (general formula [10]: X=O and Y=ClO$_4$);
4-methyl-2,6-diphenylthiapyrylium iodide (general formula [10]: X=S and Y=I);
4-methyl-2,6-diphenylthiapyrylium perchlorate (general formula [10]: X=S and Y=ClO$_4$);
4-(4-N,N-dimethylaminophenyl)-2,6-diphenylpyrylium iodide (general formula [11]: X=O and Y=I);
4-(4-N,N-dimethylaminophenyl)-2,6-diphenylpyrylium perchlorate (general formula [11]: X=O and Y=ClO$_4$);
4-(4-N,N-dimethylaminophenyl)-2,6-diphenylthiapyrylium iodide (general formula [11]: X=S and Y=I);
4-(4-N,N-dimethylaminophenyl)-2,6-diphenylthiapyrylium perchlorate (general formula [11]: X=S and Y=ClO$_4$);
2-phenyl-4,6-bis(4-N,N-dimethylaminophenyl)pyrylium iodide (general formula [12]: X=O and Y=I);
2-phenyl-4,6-bis(4-N,N-dimethylaminophenyl)pyrylium perchlorate (general formula [12]: X=O and Y=ClO$_4$);
2-phenyl-4,6-bis(4-N,N-dimethylaminophenyl)thiapyrylium iodide (general formula [12]: X=S and Y=I);
2-phenyl-4,6-bis(4-N,N-dimethylaminophenyl)thiapyrylium perchlorate (general formula [12]: X=S and Y=ClO$_4$);
4-phenyl-2,6-bis(4-N,N-dimethylaminophenyl)pyrylium iodide (general formula [13]: X=O and Y=I);
4-phenyl-2,6-bis(4-N,N-dimethylaminophenyl)pyrylium perchlorate (general formula [13]: X=O and Y=ClO$_4$);
4-phenyl-2,6-bis(4-N,N-dimethylaminophenyl)thiapyrylium iodide (general formula [13]: X=S and Y=I);
4-phenyl-2,6-bis(4-N,N-dimethylaminophenyl)thiapyrylium perchlorate (general formula [13]: X=S and Y=ClO$_4$);
2,4,6-tris(4-N,N-dimethylaminophenyl)pyrylium iodide (general formula [14]: X=O and Y=I);
2,4,6-tris(4-N,N-dimethylaminophenyl)pyrylium perchlorate (general formula [14]: X=O and Y=ClO$_4$);
2,4,6-tris(4-N,N-dimethylaminophenyl)thiapyrylium iodide (general formula [14]: X=S and Y=I);
2,4,6-tris(4-N,N-dimethylaminophenyl)thiapyrylium perchlorate (general formula [14]: X=S and Y=ClO$_4$);
2,4,6-triphenylpyrylium iodide (general formula [15]: X=O and Y=I);
2,4,6-triphenylpyrylium perchlorate (general formula [15]: X=O and Y=ClO$_4$);
2,4,6-triphenylthiapyrylium iodide (general formula [15]: X=S and Y=I); and
2,4,6-triphenylthiapyrylium perchlorate (general formula [15]: X=S and Y=ClO$_4$).

Incidentally, in the compounds represented by the general formula [1], at least one hydrophilic group such as a carboxyl group and sulfonate group may be introduced into at least one substituent of the pyrylium ring to enhance the solubility of the compounds to aqueous medium which may be used for detection or quantification of target nucleic acids.

As to a pyrylium dye compound itself, research has been conducted since the beginning of the 20th century, and a large number of articles and authorized publications have been issued. Some of the specific examples of pyrylium dye compounds used in the present invention have been synthesized by R. Wizinger, et al. (*Helv. Chim. Acta*, 39, 5, 1956), N. Yamamoto, et al. (EP 603,783 A1), and others. Further, the fluorescent properties of pyrylium dye compounds are described in the authorized publication "Advance in Heterocycle Chemistry supplement 2 Pyrylium Salt" edited by A. R. Katrizky, the aforementioned European patent publication, the specifications of U.S. Pat. Nos. 4,555,396 and 4,840,784, and others.

Additionally, the Inventors have already found that the pyrylium compounds represented by the above formula [1]

can serve as intercalators (*Nucleic Acid Symposium Series*, No. 29, 83–84, 1993), and have conducted research on processes for quantifying double-stranded nucleic acids based on fluorescent methods using such pyrylium compounds (*Nucleic Acids Research*, 23, 8, 1445–1446, 1995).

The literature relating to pyrylium dye compounds, including the above publications and articles, however, has no description concerning the chemiluminescent properties thereof.

The pyrylium compounds represented by the above-described general formula [1] exhibit chemiluminescent efficiency equal to or more than that of conventional chemiluminescent compounds, and some of such pyrylium compounds exhibit extremely high chemiluminescent efficiency.

Further, the pyrylium compound represented by the general formula [1] is stable even when being intercalated into double-stranded nucleic acids, and not readily separated from the double-stranded nucleic acid. Moreover, such a pyrylium compound is intercalated into a double-stranded nucleic acid in the ratio of one molecule of the compound to approximately 25 base pairs of the double-stranded nucleic acid (ethidium bromide is intercalated in the ratio of one molecule of EB to approximately 4 base pairs). This characteristic is greatly effective in removing detection noise derived from short double-stranded nucleic acid fragments generated by mismatch. Additionally, since short double-stranded nucleic acid portion contained in tRNA and rRNA is not detected, tRNA and rRNA can be directly used as the target nucleic acid. In the above point of view, the pyrylium compounds represented by the general formula [1] are regarded as more preferable.

In the case that the chemiluminescent compound which exhibits chemiluminescence even in a free state, namely, even when not associated with a double-stranded nucleic acid, is used, and the generated chemiluminescence raises the background level of the detection system, the free molecules of the compound is preferably removed from the luminescent reaction system by, for example, a washing treatment. Also in this case, it is preferable to use a chemiluminescent compound capable of being associated with the double-stranded nucleic acid by intercalation, since intercalation achieves more secure association between them.

If the conditions for being emitted luminescence from the chemiluminescent compound are set such that only the chemiluminescent compound associated with the double-stranded nucleic acid or only the chemiluminescent compound having undergone association with the double-stranded nucleic acid can emit luminescence, the above-mentioned washing treatment or the like can be omitted, the entire detecting process can be simplified, and the background can be effectively reduced to improve the detection sensitivity. Such conditions can be achieved by selecting a chemiluminescent compound satisfying the above-described properties, appropriately designing the physical and chemical conditions of the reaction system, or the like.

More specifically, a chemiluminescent compound capable of taking two structures "A" and "B", the structure "A" being taken before the association with the double-stranded nucleic acid, and never cause the compound to emit luminescence, and the structure "B" being taken when the compound is associated with the double-stranded nucleic acid, and causes the compound to emit luminescence, may preferably be used. Such a compound has clear threshold between states for emitting luminescence or not, thus the target nucleic acid can be detected in high sensitivity, and in remarkable S/N ratio.

For such a chemiluminescent compound, as the mode for association with the double-stranded nucleic acid, groove binding and intercalation etc. can be considered, and the chemiluminescent compound capable of being intercalated into the double-stranded nucleic acid is more preferable. When the chemiluminescent compound can serve as an intercalator, the environment surrounding the chemiluminescent compound changes. For example, when the chemiluminescent compound and the double-stranded nucleic acid are in an aqueous medium, the environment surrounding the compound changes to be more hydrophobic by intercalation. In addition, the structure of the chemiluminescent compound changes. The degree of the structural change by intercalation is higher than that by other association modes such as groove-binding, and such structural change is preferred as structural change by association employed in the present invention.

In view of structure, it is considered that the compound represented by the general formula [1] is markedly different from other intercalators, such as ethidium bromide. Since ethidium bromide has a condensed-ring structure as its central structure, it emits luminescence even before intercalation. In contrast, the compound represented by the general formula [1] has a structure which permits the compound to exhibit luminescence only when associated with double-stranded nucleic acid, or only when associated with double-stranded nucleic acid and placed under appropriate conditions for causing the luminescent reaction.

The following is considered as an explanation for such luminescent properties achieved by such specific compound structures. Each of the compound represented by the general formula [1] has no condensed-ring structure. Even if the pyrylium ring of the compound has one or more aromatic rings as substituents, such aromatic rings are bonded to the pyrylium ring by single bonds. Due to this, in a free-state where the compound is not intercalated with a double-stranded nucleic acid, each substituent of the compound is single-bonded to the pyrylium ring as a base-skeleton at an angle of a few tens degrees, and the resulting structure rarely permits the compound to exhibit luminescence. When the compound is intercalated and inserted between two oligonucleotides of the double-stranded nucleic acid, the steric positional-relationship between the pyrylium ring and each substituent is varied such that the angle between them decreases, namely, they are disposed on a common plane, and the resulting structure permits the compound to readily exhibit luminescence. According to such an mechanism, the compounds represented by the formula [1] is considered to exhibit the non-luminescent properties in the absence of double-stranded nucleic acids.

In some cases, the compound represented by the general formula [1] exhibits chemiluminescence even in the absence of the double-stranded nucleic acid when being solved into some organic solvents, especially in highly-viscous organic solvents such as dimethyl phthalate, in the presence of hydrogen peroxide and bisdinitrophenyl oxalate. In case of employing an aqueous medium instead of the organic solvents, however, the compound does not exhibit chemiluminescence in the absence of the double-stranded nucleic acid even in the presence of a luminescence-inducing reagent.

Accordingly, when such a pyrylium compound represented by the formula [1] is intercalated into a double-stranded nucleic acid in an aqueous medium, such as water, an aqueous buffered solution (a phosphate buffered solution, a Tris buffered solution etc.) in the presence of a luminescence-inducing reagent, only the pyrylium compound intercalated into the double-stranded nucleic acid can exhibit chemiluminescence. Such a system is extremely effective in achieving highly sensitive and simple detection of target nucleic acids and precise quantification of the same.

The mechanism of chemiluminescence is basically considered as follows: A certain substance is chemically excited into an excitation state, and a luminescent energy is discharged when the substance returns to the ground state. Various chemiluminescent reaction systems have been developed, and the following are typical examples of them.

(1) A system in which luminol or a luminol derivative is excited by hydrogen peroxide in the presence of a catalyst, and emits luminescence when it returns to the ground state.

(2) A system in which N-methylacridinium is excited by hydrogen peroxide in an alkaline condition, and emits luminescence when it returns to the ground state.

(3) A system in which lucinigen is excited by a reductive substance in an alkaline condition, and emits luminescence when it returns to the ground state.

(4) A system in which an oxalic ester or derivative thereof is converted into an excited intermediate by a peroxide, a coexisting fluorochrome is excited by the energy discharged when the intermediate is decomposed, and the excited fluorochrome emits chemiluminescence when it returns to the ground state.

Although in the present invention, various luminescent reaction systems including the above systems (1) to (4) can be employed, the system (4) is more preferable. For example, when a pyrylium compound represented by the general formula [1] is used as a chemiluminescent compound, a combination of an oxalic ester or derivative thereof and a peroxide is preferred as a luminescence-inducing reagent. Examples of an oxalic ester and derivative thereof used in such a luminescence-inducing reagent includes oxalates such as the compounds respectively represented by the following formulae [16] to [24], and oxamides such as the compounds respectively represented by the following formulae [25] to [30].

[16]
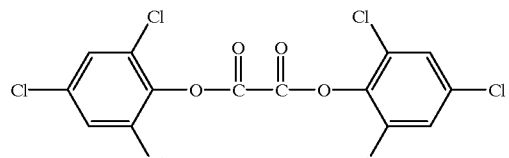

[17]
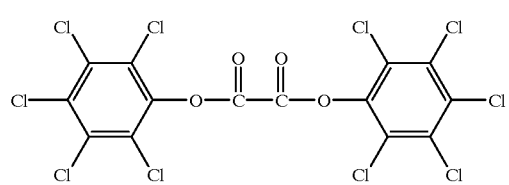

[18]
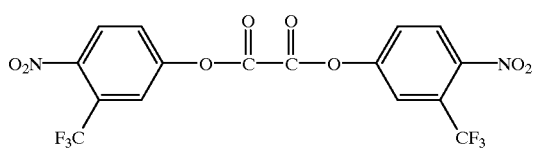

[19]
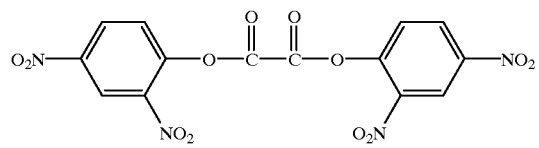

[20]
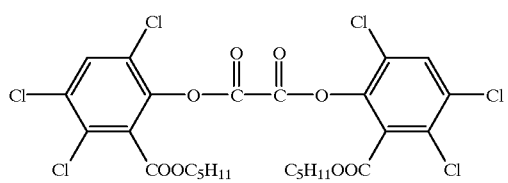

[21]
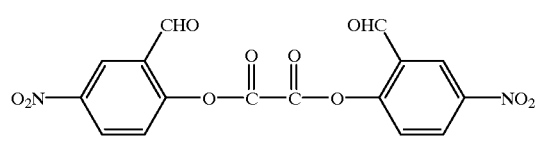

[22]
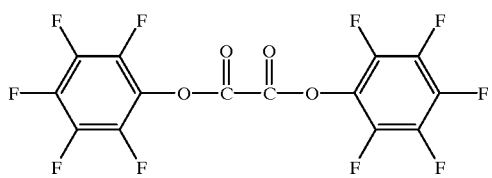

[23]
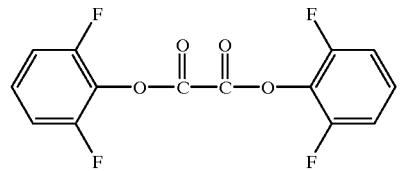

[24]
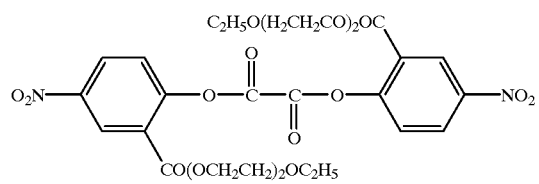

[25]
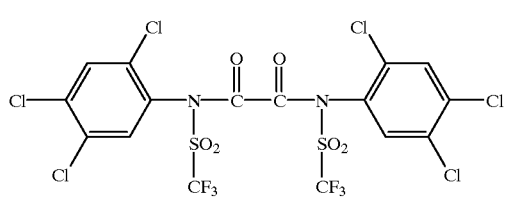

[26]
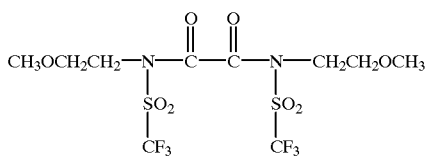

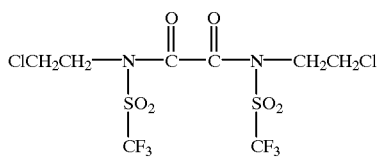

[27]

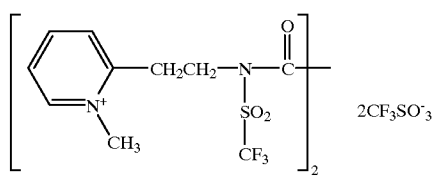

[28]

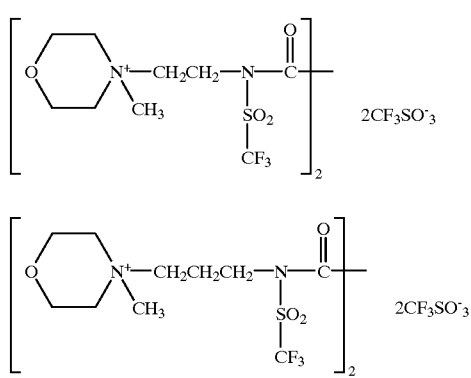

[29]

[30]

Further, any peroxide can be used in combination with such an oxalic ester without any special limitation so long as it can derive an exited intermediate from the oxalic ester. A preferred example of such a peroxide is hydrogen peroxide.

Chemiluminescence can be detected in an appropriate medium capable of causing the chemiluminescent compound associated with a double-stranded nucleic acid to emit luminescence. An aqueous medium is preferred as a medium, since the medium can prevent the chemiluminescent compound in free state from emitting luminescence in the presence of a reagent causing the compound to emit luminescence. Examples of such a medium include water, aqueous buffered solutions, such as a phosphate buffered solution, Tris buffered solution etc. The pH of such an aqueous medium preferably falls within a range in which the double-stranded nucleic acid and the chemiluminescent compound are stable. In the case of the compound represented by the general formula [1], the preferred pH range is from 5.0 to 8.0. Incidentally, although some of the compounds represented by the general formula [1] are capable of exhibiting chemiluminescence in a highly viscous organic solvent such as dimethyl phthalate in the presence of a luminescence-inducing reagent such as the combination of hydrogen peroxide and bisdinitrophenyl oxalate (Compound 19) even in the absence of a double-stranded nucleic acid, such compounds do not exhibit chemiluminescence in the case where an aqueous medium is used instead of such an organic solvent.

If necessary, an organic solvent soluble in such an aqueous medium may be added in an amount not affecting achievement of the object of the present invention, in order to further improve the solubility of the reagents in the aqueous medium. Examples of such an organic solvent include methanol, ethanol, acetonitrile, dimethylformamide, and dimethylsulfoxide. Actually used organic solvent and its amount are appropriately determined depending on the combination of the chemiluminescent compound and the luminescence-inducing reagent. In general, the amount of such organic solvents should preferably fall within the range from 2 to 50% by volume, and more preferably, the lower limit of the range should be 5% by volume and the upper limit of the range should be 20% by volume, and further more preferably, the upper limit of the range should be 10% by volume.

One of the preferable embodiments of a process for detecting/quantifying a target nucleic acid according to the present invention will now be described. In case that the target nucleic acid is a single-stranded nucleic acid having a specific base sequence, a probe nucleic acid having a base sequence complementary to the specific base sequence is prepared. Then, the target nucleic acid and the probe nucleic acid are hybridized to form a double-stranded nucleic acid, and then a chemiluminescent compound represented by the formula [1] is inserted into the double-stranded nucleic acid as an intercalator. Subsequently, chemiluminescence from the intercalated chemiluminescent compound is detected/measured in the conditions where only the chemiluminescent compound molecules inserted into the double-stranded nucleic acid can exhibit chemiluminescence.

In the above-described case, since chemiluminescence is utilized for detection/quantification of the double-stranded nucleic acid, the previously described problems with fluorescent methods can be solved. Moreover, since the chemiluminescent compound can be inserted into the hybrid nucleic acid after the hybridization step, the probe nucleic acid does not require being previously coupled with a labelling substance. Due to this, the probe nucleic acid can be prevented from destabilizing which may occur in the case where the probe nucleic acid is labelled.

Further, in case of requiring intense luminescence, the length of the double-stranded portion of a hybrid formed between the target single-stranded nucleic acid and the probe nucleic acid may be extended by using so-called extension reaction. By extending the length of the double-stranded portion of the hybrid, a portion where the chemiluminescent compound is associated with in the hybrid, can be enlarged. That is, the number of a molecular of the chemiluminescent compound associated with the hybrid, increases.

Accordingly, detection of the double-stranded nucleic acid can be further facilitated, and the detection sensitivity can be enhanced. In the case that the probe nucleic acid is 200-mer and the target single-stranded nucleic acid is form 200-mer to 1,000-mer, for example, the detection sensitivity can be improved in one or two orders of magnitude, and some cases in three orders of magnitude in proportion to the extension of the length of the double-stranded portion of the hybrid.

In the step for hybridizing the target single-stranded nucleic acid and the probe nucleic acid, the target nucleic acid or probe nucleic acid may be immobilized on a solid phase previous to the succeeding reactions. According to this manner, for example, the free chemiluminescent compound molecules not inserted into the double-stranded nucleic acid can readily be separated from the chemiluminescent compound molecules inserted into the double-stranded nucleic acid.

Immobilization of the target or probe nucleic acid to a solid phase can be carried out according to a publicly-known method selected depending on the type of the immobilized nucleic acid, the material of the solid phase, and the like. The carrier material of the solid phase is not especially limited so long as it achieves the desired immobilized state of the target or probe nucleic acid, the hybridization between the target nucleic acid and the probe nucleic acid, the association between the resulting hybrid and the chemiluminescent compound, and luminescence from the chemiluminescent compound. Dissimilar to calorimetric methods and fluorescent methods, even carrier materials which intensely scatter the detected luminescence, such as a nitrocellulose filter or a nylon filter, can be used in the present invention.

In view of easy measurement of luminescence for quantification, plastic plates such as microtiter plates which can be used in microplate readers are preferred as such solid phases. Immobilization of the nucleic acid to a microtiter plate can, for example, be achieved based on covalent binding or physical binding, though covalent binding is preferable in view of easy operation and secure detection. Such immobilization based on covalent binding can be achieved, for example, by covalent-binding functional groups on the surface of the microtiter plate and functional group of the nucleic acid, as disclosed in Japanese Patent Laid-open No. 7-506482.

For the reaction between the target nucleic acid and the probe nucleic acid in a sample, an ordinary solid-phase hybridization method can be employed.

Meanwhile, as described above the structure of the probe nucleic acid may be designed such that the hybrid formed on a solid phase with the target nucleic acid and the probe nucleic acid comprises a double-stranded portion and a single-stranded portion. By this means, a double-stranded portion in the hybrid can be extended using a single-stranded portion in the hybrid as a template base sequence, and as a result, the detection sensitivity can be further improved. The extension of the double-stranded portion can also be achieved by a publicly-known method. Incidentally, when the target nucleic acid is mRNA (for example, total mRNA) extracted from an organism, the oligoriboadenylic acid portion present at the 3 prime end of any mRNA can be preferably utilized. More specifically, an oligo- or polydeoxyribothymidylic acid, or an oligo- or polyuridylic acid is preferably used as the probe nucleic acid, and the hybrid portion (double-stranded portion) comprising the probe nucleic acid and the oligoriboadenylic acid portion of the target nucleic acid is preferably used as the starting site for the extension of the double-stranded portion.

According to the present invention, a target nucleic acid is detected through detection of chemiluminescence. The present invention, therefore, provides a possibility to achieve extremely highly sensitive detection of target nucleic acids. For example, if detection of the luminescence from one molecule of the chemiluminescent compound can be actualized by, for example, employing a photo-counting method, even a nucleic acid associated with only one molecule of the chemiluminescent compound can be detected.

The nucleic-acid-detecting process according to the present invention can also suitably be applied to quantification of a target nucleic acid. For example, standard target-nucleic-acid samples of several concentrations are subjected to detection, a calibration curve is obtained from the relationship between luminescent intensity and target-nucleic-acid concentration, an unknown sample is then subjected to detection, and the target nucleic acid in the unknown sample is quantified from the luminescent intensity observed in the detection by referring the calibration curve.

The present invention will be further illustrated in detail with reference to the examples below.

EXAMPLE 1
Measurement of Luminescence Wavelength and Relative Luminescence Intensity
(1) Preparation of Reagent Solutions
A. 0.2 M $H_2O_2$ Solution
   2 milliliters of a 30% by weight $H_2O_2$ solution was added to a mixture solution comprising 5 ml of dimethylsulfoxide and 93 ml of a 10 mM phosphate buffered solution (pH 6.0).
B. Chemiluminescent Compound Solution
   Necessary amounts of Compounds "a" to "r" listed in Table 2 were individually solved in appropriate volumes of dimethylsulfoxide. The resulting solutions were then 20-fold-diluted with a 10 mM phosphate buffered solution (pH 6.0) such that the concentration of the chemiluminescent compound in each diluted solution fell within 5 to 50 $\mu$M, and the absorbance of the solution at the wavelength for the maximum absorption in the visible light region was 0.5.
C. 2.5 mM Bisdinitrophenyl Oxalate (DNPO) Solution 42 milligrams of DNPO was dissolved in a mixture comprising 4 ml of dimethylsulfoxide and 36 ml of a 10 mM phosphate buffered solution (pH 6.0).
D. Double-Stranded Nucleic-Acid Solution having a Base-Pair Concentration of 100 nM
   Salmon Testea DNA (Sigma, 10 mg/ml) was sonicated into double-stranded nucleic-acid fragments having an average length of 200 base pairs, and then stepwisely diluted with a 10 mM phosphate buffered solution (pH 6.0) to obtain a double-stranded nucleic-acid solution having a base-pair concentration of 100 nM.
(2) Detection of Chemiluminescence
   Each 400 $\mu$l of above-prepared reagents A and B were placed in a quartz cell for fluorescence measurement having a size of 1 cm×1 cm (optical path length×optical path width). After being well-mixed, each 400 $\mu$l of reagents C and D were further added and immediately mixed to intercalate the chemiluminescent compound into the double-stranded nucleic acid, and the resulting luminescent spectrum was examined using an optical multidetection system IMUC-7000 (Otsuka Electronic Industries, Co., Ltd.). For each chemiluminescent compound the luminescence wavelength where the compound exhibited the maximum luminescent intensity, and the relative luminescence intensity are shown in Table 2. The relative luminescence intensity ($L_n$) is calculated from the following equation.

$$L_n \times [I_n/I_a] \times 100$$

(In the above equation, $I_n = [rI_n/C_n]$, wherein $rI_n$ is the really measured luminescent intensity, $C_n$ is the concentration of the chemiluminescent compound, and n is the ID symbol for the compound.)

TABLE 2

| Compound ID | General Formula | X | Y | Luminescence Wavelength (nm) | Relative Luminescence Intensity (integral value) |
|---|---|---|---|---|---|
| a | [7] | O | I | 645 | 100 |
| b | [7] | S | I | 700 | 25 |
| c | [8] | O | $ClO_4$ | 435 | 130 |
| d | [8] | S | $ClO_4$ | 465 | 30 |
| e | [9] | O | I | 670 | 40 |
| f | [9] | S | I | 720 | 15 |
| g | [10] | O | $ClO_4$ | 440 | 50 |
| h | [10] | S | $ClO_4$ | 500 | 17 |
| i | [11] | O | I | 630 | 10 |
| j | [11] | S | I | 690 | 5 |
| k | [12] | O | I | 690 | 14 |
| l | [12] | S | I | 745 | 5 |
| m | [13] | O | I | 720 | 23 |
| n | [13] | S | I | 770 | 8 |
| o | [14] | O | I | 700 | 30 |

TABLE 2-continued

| Compound ID | General Formula | X | Y | Luminescence Wavelength (nm) | Relative Luminescence Intensity (integral value) |
|---|---|---|---|---|---|
| p | [14] | S | I | 760 | 12 |
| q | [15] | O | ClO$_4$ | 450 | 42 |
| r | [15] | S | ClO$_4$ | 470 | 14 |

Incidentally, no chemiluminescence could be observed in an experiment conducted similar to the above except for using a 10 mM phosphate buffered solution (pH 6.0) instead of reagent D.

As is obvious from the results, the compounds listed in Table 2 exhibit chemiluminescence only in the presence of a double-stranded nucleic acid under the condition that an aqueous medium is used, and are useful for detection of double-stranded nucleic acids. Further, they exhibit satisfactory luminescence intensities, though the luminescence wavelengths are different depending on the compounds.

EXAMPLE 2
Quantification of Double-Stranded Nucleic Acid
(1) Preparation of Reagent Solutions
E. Chemiluminescent Compound Solution A necessary amount of Compound "c" listed in Table 2 above was solved in an appropriate volume of dimethylsulfoxide. The resulting solution was then 20-fold-diluted with a 10 mM phosphate buffered solution (pH 6.0) to prepare a chemiluminescent compound solution of 10 µM.

F. Double-Stranded Nucleic-Acid Solution

Reagent D prepared in Example 1 was stepwisely diluted with a 10 mM phosphate buffered solution (pH 6.0) to obtain double-stranded nucleic acid solutions having base-pair concentrations of 0.05, 0.5, 5, 50 and 500 fM, respectively.

(2) Measurement of Chemiluminescence Intensity

Each 200 µl of reagent A prepared in Example 1 and the above-prepared reagents E and F were placed in a polystyrene cell for Luminometer 1251 manufactured by BioOrbit Co., Ltd. After the cell was placed in a sample chamber of the luminometer, 400 µl of reagent C prepared in Example 1 was further added using an adjunct dispenser while being consistently stirred the mixture by a stirrer disposed in the luminometer. Luminescence intensity of each sample was measured from 5 to 15 sec. after the start of the operation of the dispenser (including the time when the maximum luminescence intensity was exhibited), and the integral value of luminescence intensity was obtained. The results are shown in FIG. 1. [In FIG. 1, for the sake of convenience, the blank value observed when an equal volume of a 10 mM phosphate buffered solution (pH 6.0) was added instead of the double-stranded nucleic-acid solution is plotted as the value when the concentration of hydrogen peroxide is 0.001 fM.] As is obvious from FIG. 1, Compound "c" is applicable to quantification of double-stranded nucleic acids, and the detection limit of the system using it was approximately 0.1 fM (in terms of base pair).

EXAMPLE 3
Quantification of Double-Stranded Nucleic Acid

Figure 2:
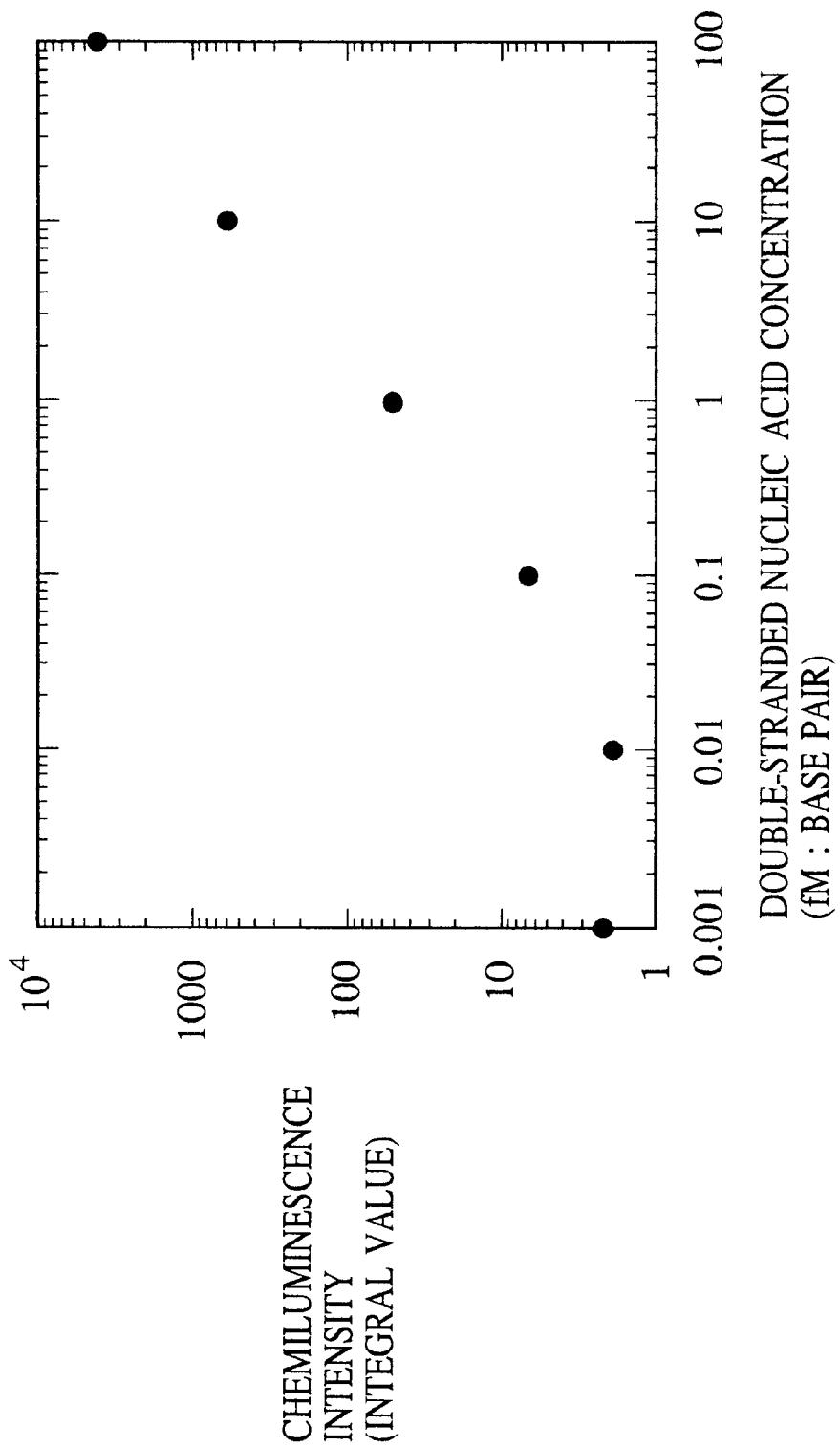

A double-stranded nucleic acid was detected in the same manner as Example 2 except that Compound "a" was used instead of Compound "c". The results are shown in FIG. 2. The detection limit of the system using Compound "a" was also approximately 0.1 fM (in terms of base pair).

EXAMPLE 4
Quantification of Double-Stranded Nucleic Acid

Figure 3:
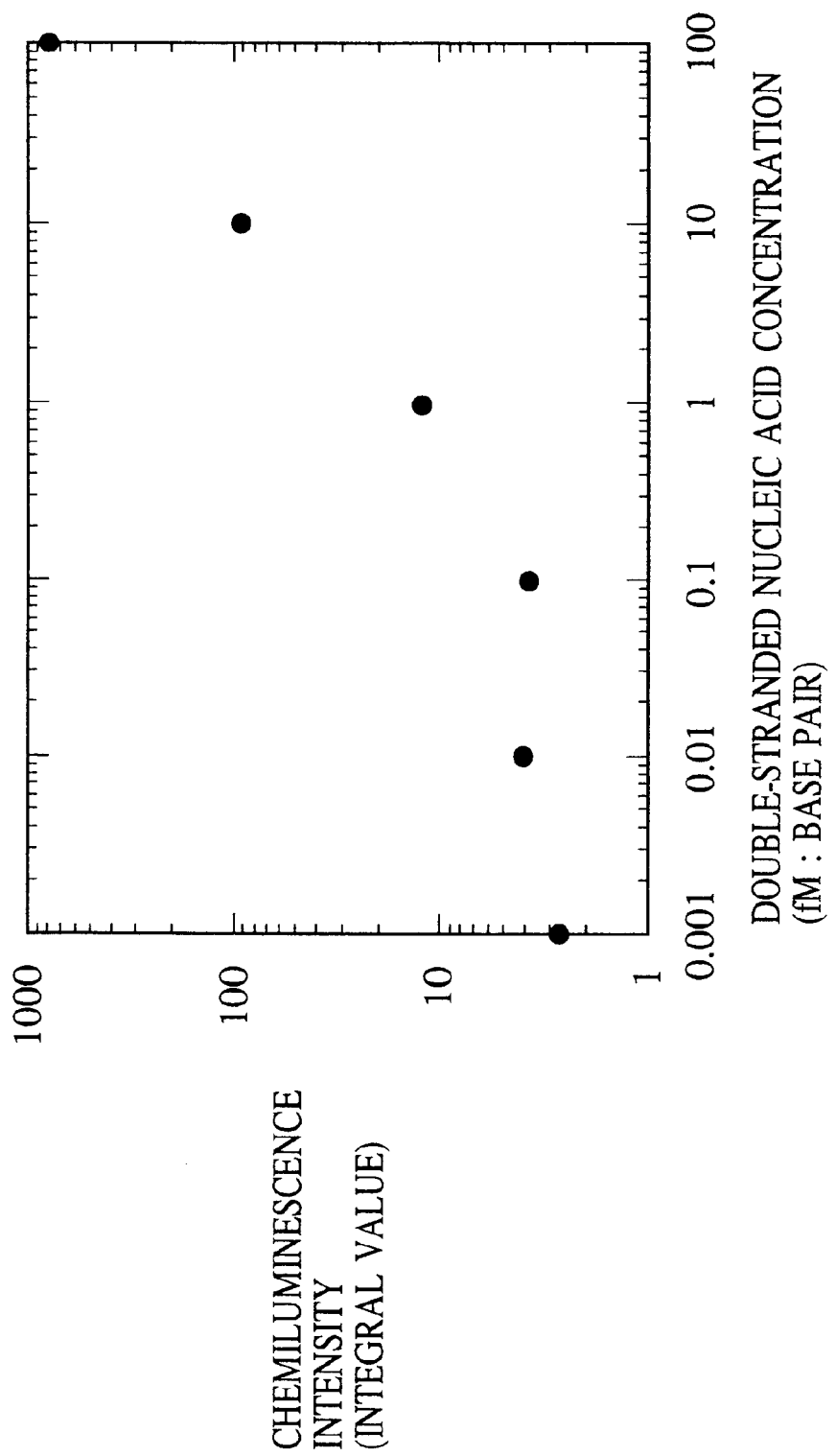

A double-stranded nucleic acid was detected in the same manner as Example 2 except that Compound "p" was used instead of Compound "c". The results are shown in FIG. 3. The detection limit of the system using Compound "p" was also approximately 0.1 fM (in terms of base pair).

EXAMPLES 5–14
Detection of Target Single-Stranded Nucleic Acid

In the below-described Examples 5 to 14, the operation to hybridize the sample and the probe nucleic acid was based on the method described in the publication, Saibo Kogaku (Cell Engineering) extra, "Baio Jikken Irastoreiteddo (Biology Experiments Illustrated), Vol. 2, Idenshi Kaiseki no Kiso (Fundament of Genetic Analysis)" (pp. 137–152, published on Sep. 25, 1995 by Shujun-sha Co., Ltd.), and the operation for chemiluminescent reaction is based on the method described in the publication, "Seibutsuhakkou to Kagakuhakkou, Kiso to Jikken (Bioluminescence and Chemiluminescence, Fundament and Experiments)" (pp. 257–258, published on Jan. 10, 1989 by Hirokawa Publishing Co.).

Further, the reagents commonly used in Examples 5 to 14 were prepared as follows.
(1) Hybridization Buffered Solution 50 milliliter of a 1 M Church phosphate buffered solution (pH 7.2), 200 µl of a 500 mM EDTA solution, and 7 g of sodium dodecylsulfate (SDS) powder were mixed, and pure water was added to the mixture such that the entire volume of the mixture was 100 ml, thus obtaining a buffered solution for hybridization.

(2) Washing Solution 40 milliliter of a 1 M Church phosphate buffered solution (pH 7.2), 100 ml of a 10% by weight SDS solution, and 860 ml of pure water were mixed to obtain a washing solution.

EXAMPLE 5
Detection of Single-Stranded DNA Using Acridine Orange
(1) Hybridization 7 sample solutions were obtained which contained 0.001, 0.01, 0.1, 1.0, 10, 100, and 1000 attomoles of a single-stranded DNA M13mp18 (manufactured by Takara Shuzo Co., Ltd.), respectively, in each 10 µl of a TE buffered solution (pH 7.5).

Next, a blotting membrane (trade name Hybond N$^+$, manufactured by AMERSHAM INTERNATIONAL, plc.) was cut into 7 circle sheets having a diameter of 16.5 mm, and impregnated at the center with the above-prepared sample solutions one by one. After left standing at room temperature for 30 min. to be dried, the membrane sheets were washed in a 2×SSC buffered solution for 60 sec., and dried at 80° C. for 2 hours to immobilize the samples to the membrane sheets, respectively.

The membrane sheets on which the samples were respectively immobilized were respectively placed on the bottoms of wells of a 24-well tissue-culture flat-bottom microplate (manufactured by Corning Laboratory Science Company). After each well was filled with 1 ml of the hybridization buffered solution preheated at 60° C., prehybridization was carried out at 60° C. for 5 min.

Next, each 5 µl of a TE buffered solution containing 1 picomole of a probe DNA, M13 Primer-M4 d SEQ ID No. 1 (GTTTTCCCAGTCACGAC) (manufactured by Takara Shuzo Co., Ltd.), which was previously subjected to a heat-shock treatment at 90° C. was added to each well. In this state, the microplate was covered, and hybridization was carried out at 60° C. for 18 hours while shaking.

After hybridization, the solution was removed from each well, and the wells were washed with each 1 ml of the washing solution at 60° C. for 5 min. This washing procedure was repeated 3 times, and the wells were further washed with each 1 ml of a TE buffered solution at room temperature 2 times. The TE buffered solution was then removed from each well, and the resulting microplate was subjected to the succeeding operation (2) described below.

(2) Detection of Luminescence

The following reagents were used for detection of luminescence.

i) 0.1 M $H_2O_2$ Solution

One milliliter of a 30% by weight $H_2O_2$ aqueous solution was added to a mixture comprising 20 ml of t-butyl alcohol and 80 ml of dimethyl phthalate, and then well mixed to prepare a 0.1 M $H_2O_2$ solution.

ii) Chemiluminescent Compound Solution

A solution of 0.1 mM (3 mg/10 ml) acridine orange in dibutyl phthalate was 1000-fold-diluted to prepare a 0.1 $\mu$M chemiluminescent compound solution.

iii) 2.3 mM Bis(2,4,6-trichlorophenyl)Oxalate (TCPO; Compound 56) Solution

In 40 ml of dimethyl phthalate, 45 mg of TCPO was dissolved to prepare a solution of Compound 56.

Further, an automatic fluorescence-measuring system, CytoFluor II (manufactured by Japan Perceptive Limited), was used as a measurement apparatus, in which the portion around the excitation filter was screened with a screening plate such that excitation light cannot reach the measuring position, and the portion around the fluorescence filter was made to be penetrable such that any luminescence could be detected. The gain of the detector was set at 80.

Figure 4:
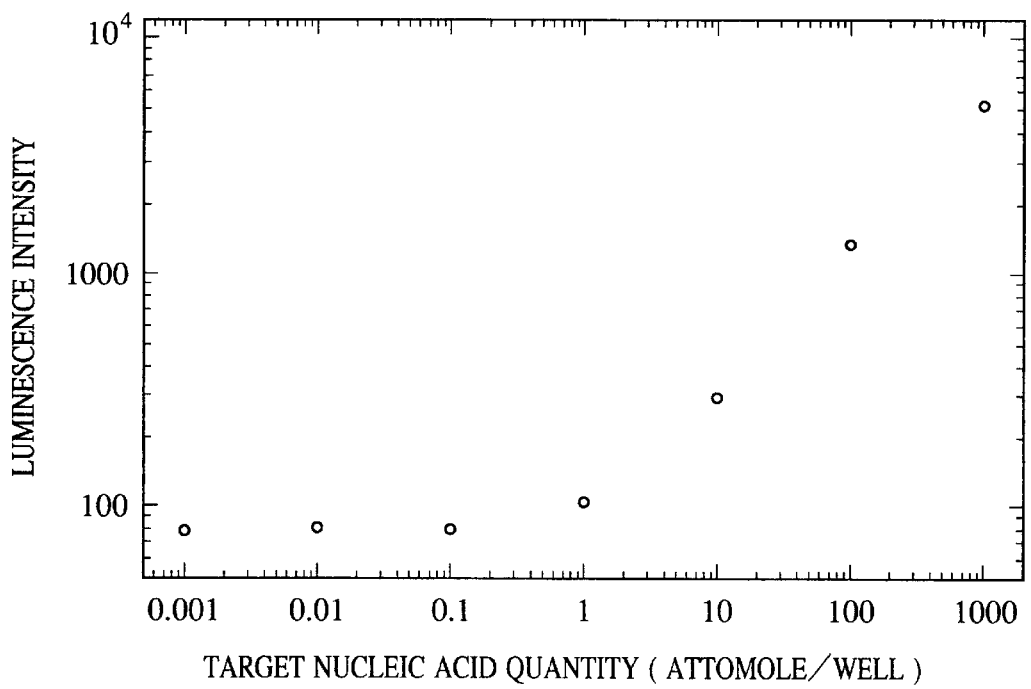

Each well of the microplate subjected to the above-described operation (1) was washed with 1 ml of dimethyl phthalate, then filled with 1 ml of the chemiluminescent compound solution ii) and left standing at room temperature for 5 min., and after the removal of the solution ii), washed with 1 ml of dimethyl phthalate 3 times. After the removal of the dimethyl phthalate as a washing solution, each 600 $\mu$l of the solution i) and each 400 $\mu$l of the solution iii) were added to each of the wells and immediately mixed. Succeedingly, 10 sec. after the addition of the solutions i) and iii) the luminescence intensity was measured while being consistently stirred by a stirrer disposed in the measurement apparatus. The results are shown in FIG. 4. As is obvious from FIG. 4, the detection sensitivity was approximately 1.0 attomole.

For comparison, a luminescence measurement was carried out in a manner similar to the above except that the washing treatment after the addition of the chemiluminescent compound solution ii) to the wells was omitted. Satisfactory measurement results could not, however, be obtained since the background in the measurement was excessively raised.

EXAMPLE 6

Detection of Single-Stranded DNA Using 2,4,6-Triphenylpyrylium Perchlorate in Non-Aqueous Medium (1) Hybridization Hybridization, washing, and other treatments were conducted similar to the operation (1) of Example 5 above.

(2) Detection of Luminescence

The following reagents were used for detection of luminescence.

i) 0.1 M $H_2O_2$ Solution 1 milliliter of a 30% by weight $H_2O_2$ aqueous solution was added to a mixture comprising 20 ml of t-butyl alcohol and 80 ml of dimethyl phthalate, and then well mixed to prepare a 0.1 M $H_2O_2$ solution.

ii) Chemiluminescent Compound Solution A solution of 0.1 mM (4.5 mg/10 ml) 2,4,6-triphenylpyrylium perchlorate in dimethyl phthalate was 1000-fold-diluted to prepare a 0.1 $\mu$M chemiluminescent compound solution.

iii) 2.5 mM Bis(2,4-Dinitrophenyl) Oxalate (DNPO, Compound 59) Solution

In 40 ml of dimethyl phthalate, 42 mg of DNPO was dissolved to prepare the object solution.

Figure 5:
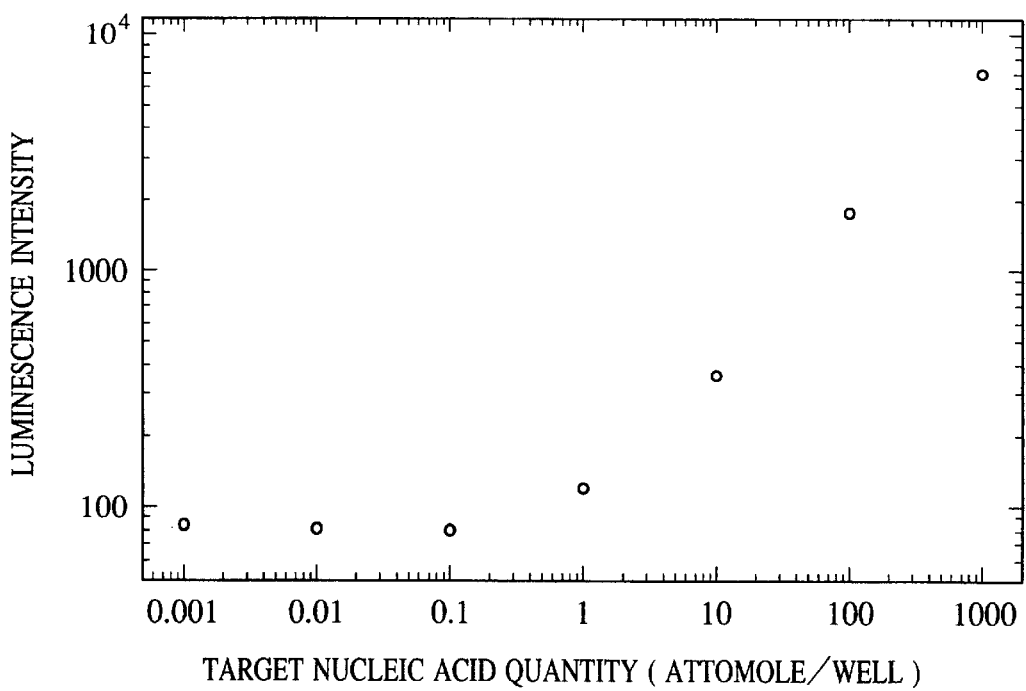

Each well of a microplate subjected to the above-described operation (1) was washed with 1 ml of dimethyl phthalate, then filled with 1 ml of the chemiluminescent compound solution ii) and left standing at room temperature for 5 min., and after the removal of the solution ii), washed with 1 ml of dimethyl phthalate 3 times. After the removal of the dimethyl phthalate, each 600 $\mu$l of the solution i) and each 400 $\mu$l of the solution iii) were added to each well and immediately mixed. Succeedingly, similar to Example 5, 10 sec. after the addition of the solutions i) and iii) the luminescence intensity was measured while being consistently stirred by a stirrer disposed in the measurement apparatus. The results are shown in FIG. 5. As is obvious from FIG. 5, the detection sensitivity was approximately 1.0 attomole.

For comparison, a luminescence measurement was carried out in a manner similar to the above except that the washing treatment after the addition of the chemiluminescent compound solution ii) to the wells was omitted. Satisfactory measurement results could not, however, be obtained since the background in the measurement was excessively raised.

EXAMPLE 7

Detection of Single-Stranded DNA Using 2-Methyl-4,6-bis (4-N,N-dimethylaminophenyl)pyrylium Iodide (1) Hybridization Hybridization and other treatments were conducted similar to the operation (1) of Example 5 above, except that the 2-time-repeated washing treatment using a TE buffered solution after the washing treatment using the above-specified washing solution was carried out using a 10 mM phosphate buffered solution (pH 6.0).

(2) Detection of Luminescence

The following reagents were used for detection of luminescence.

i) 0.2 M $H_2O_2$ Solution 2 milliliters of a 30% by weight $H_2O_2$ aqueous solution was added to a mixture comprising 5 ml of dimethylsulfoxide (DMSO) and 93 ml of a 10 mM phosphate buffered solution (pH 6.0), and then well mixed to prepare a 0.2 M $H_2O_2$ solution.

ii) Chemiluminescent Compound Solution

To 1 ml of DMSO, 4.5 mg of 2-methyl-4,6-bis(4-N,N-dimethylaminophenyl) pyrylium iodide was dissolved, and the resulting mixture was then added to and mixed with 9 ml of a 10 mM phosphate buffered solution (pH 6.0). The resulting mixture was 400-fold-diluted with a 10 mM phosphate buffered solution (pH 6.0) containing 5% by weight of DMSO to prepare a 0.25 $\mu$M chemiluminescent compound solution.

iii) 2.5 mM DNPO Solution

In a mixture comprising 4 ml of DMSO and 36 ml of a 10 mM phosphate buffered solution (pH 6.0), 42 mg of DNPO was dissolved to prepare the object solution.

Figure 6:
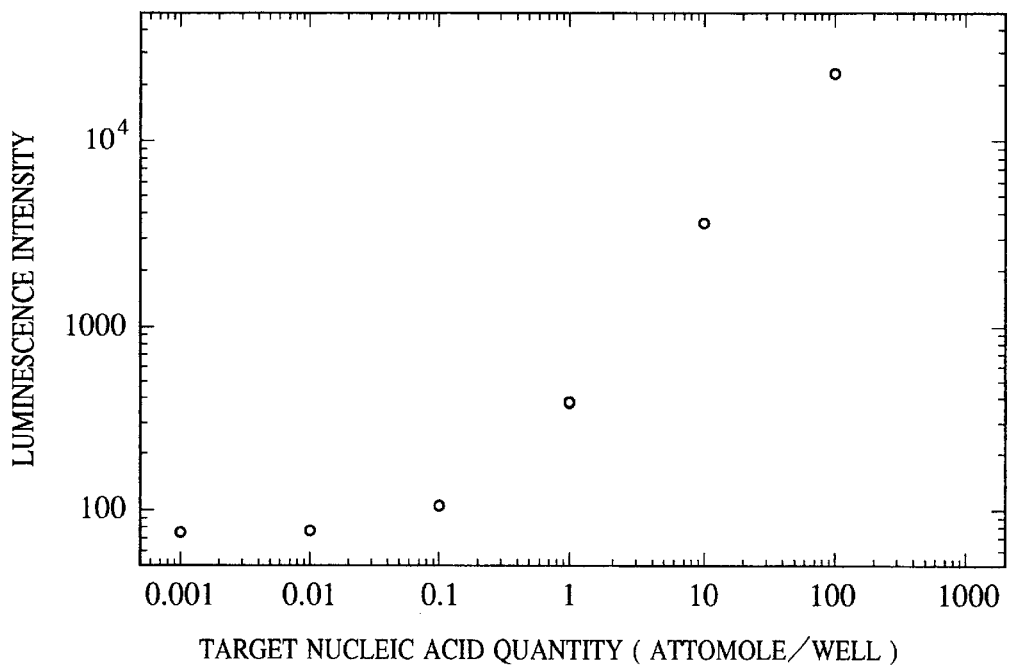

Each 400 $\mu$l of the solution ii) was added to each well of a microplate subjected to the hybridization and the washing treatments as described in the above paragraph (1), and left standing at room temperature for 5 min. to intercalate the chemiluminescent compound into the resulting double-stranded nucleic acids. After this, each 200 $\mu$l of the solution i) and each 400 $\mu$l of the solution iii) were added to each well and immediately mixed. Succeedingly, similar to Example 6, the luminescence intensity 10 sec. after the addition of the solutions i) and iii) was measured while being consistently stirred by a stirrer disposed in the measurement apparatus. The results are shown in FIG. 6. As is obvious from FIG. 6, the detection sensitivity was approximately 0.1 attomole.

EXAMPLE 8

Detection of Double-Stranded DNA Using YOYO-1

(1) Hybridization

Seven DNA solutions in Eppendorf tubes were prepared which contained 0.001, 0.01, 0.1, 1.0, 10, 100, and 1000 attomoles of a double-stranded DNA M13mp18RF (manufactured by Takara Shuzo Co., Ltd.), respectively, in each 5 μl of pure water. To each tube, 5 μl of a 1.5 M NaOH solution was added, and left standing at room temperature for 30 min. to degenerate the double-stranded DNA into single-stranded DNAs, thus obtaining 7 sample solutions.

Next, 7 circular sheets of blotting membrane in 16.5 mm-diameter (trade name Hybond N⁺, manufactured by AMERSHAM INTERNATIONAL, plc.) were prepared, and at the center of each of the sheets the above-prepared sample solution was impregnated. After left standing at room temperature for 30 min. to be dried, the membrane sheets were washed in a 2×SSC buffered solution for 60 sec. 3 times, and dried at 80° C. for 2 hours to immobilize the samples to the membrane sheets, respectively.

The membrane sheets on which the samples were respectively immobilized were respectively placed on the bottoms of wells of a 24-well tissue-culture flat-bottom microplate (manufactured by Corning Laboratory Science Company). After each well was filled with 1 ml of the hybridization buffered solution preheated at 60° C., prehybridization was carried out at 60° C. for 5 min.

Next, each 5 μl of a TE buffered solution containing 1 picomole of a probe DNA, M13 Primer M3 d SEQ ID NO. 2 (GTAAAACGACGGCCAGT) (manufactured by Takara Shuzo Co., Ltd.), which was previously subjected to a heat-shock treatment at 90° C. was added to each well. In this state, the microplate was covered, and hybridization was carried out at 60° C. for 18 hours while shaking.

After hybridization, the solution was removed from each well, and the wells were washed with each 1 ml of the washing solution at 60° C. for 5 min. This washing procedure was repeated 3 times, and the wells were further washed with each 1 ml of a TE buffered solution at room temperature 2 times. The TE buffered solution was then removed from each well, and the resulting microplate was subjected to the succeeding operation (2) described below.

(2) Detection of Luminescence

The following reagents were used for detection of luminescence.

i) 0.1 M $H_2O_2$ Solution 1 milliliter of a 30% by weight $H_2O_2$ aqueous solution was added to a mixture comprising 20 ml of t-butyl alcohol and 80 ml of dimethyl phthalate, and then well mixed to prepare a 0.1 M $H_2O_2$ solution.

ii) Chemiluminescent Compound Solution

A solution of 0.1 mM (13 mg/10 ml) YOYO-1 (manufactured by Molecular Probe Co., Ltd.) in dibutyl phthalate was 1000-fold-diluted to prepare a 0.1 μM chemiluminescent compound solution.

iii) 2.3 mM TCPO Solution

In 40 ml of dimethyl phthalate, 45 mg of TCPO was dissolved to prepare the object solution.

Figure 7:
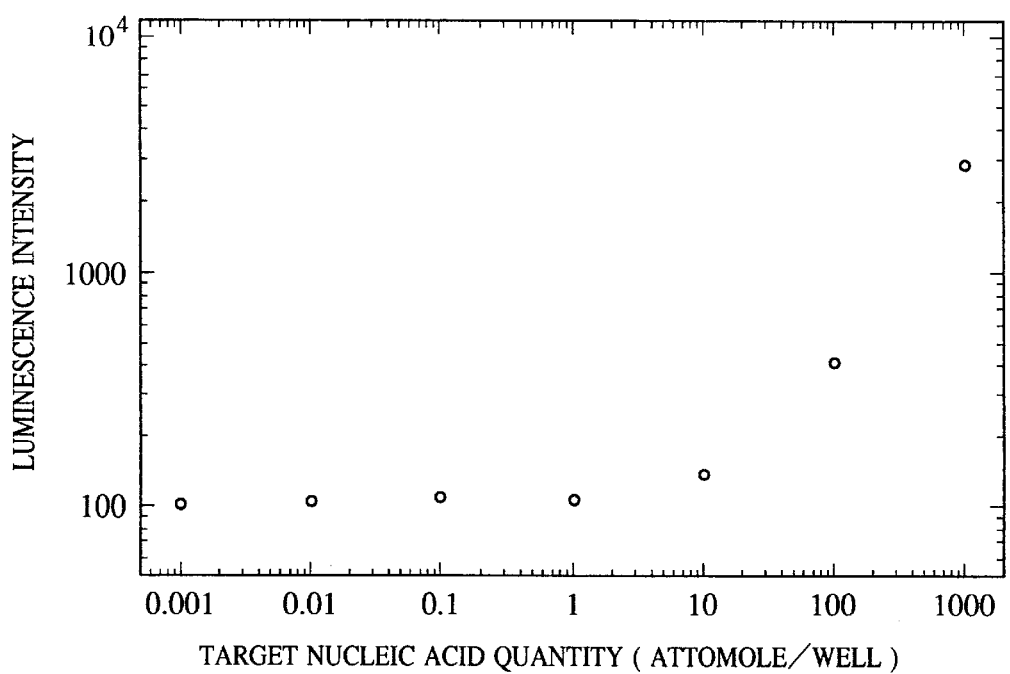

Each well of the microplate subjected to the above-described operation (1) was washed with 1 ml of dimethyl phthalate, then filled with 1 ml of the chemiluminescent compound solution ii) and left standing at room temperature for 5 min., and washed with 1 ml of dimethyl phthalate 3 times. After the removal of the dimethyl phthalate, each 600 μl of the solution i) and each 400 μl of the solution iii) were added to each well and immediately mixed. Succeedingly, similar to Example 5, 10 sec. after the addition of the solutions i) and iii) the luminescence intensity was measured while being consistently stirred by a stirrer disposed in the measurement apparatus. The results are shown in FIG. 7. As is obvious from FIG. 7, the detection sensitivity was approximately 10 attomole.

For comparison, a luminescence measurement was carried out in a manner similar to the above except that the washing treatment after the addition of the chemiluminescent compound solution ii) to the wells was omitted. Satisfactory measurement results could not, however, be obtained since the background in the measurement was excessively raised.

EXAMPLE 9

Detection of Double-Stranded DNA Using 2-Methyl 4,6-diphenylpyrylium Perchlorate in Non-Aqueous Solvent System (1) Hybridization Denaturation of the double-stranded DNA, hybridization, washing and other treatments were performed similar to Example 8 above.

(2) Detection of Luminescence

The following reagents were used for detection of luminescence.

i) 0.1 M $H_2O_2$ Solution

One milliliter of a 30% by weight $H_2O_2$ aqueous solution was added to a mixture comprising 20 ml of t-butyl alcohol and 80 ml of dimethyl phthalate, and then well mixed to prepare a 0.1 M $H_2O_2$ solution.

ii) Chemiluminescent Compound Solution

A solution of 0.1 mM (4.5 mg/10 ml) 2-methyl-4,6-diphenylpyrylium perchlorate in dibutyl phthalate was 1000-fold-diluted to prepare a 0.1 μM chemiluminescent compound solution.

iii) 2.5 mM DNPO Solution

In 40 ml of dimethyl phthalate, 42 mg of DNPO was dissolved to prepare the object solution.

Figure 8:
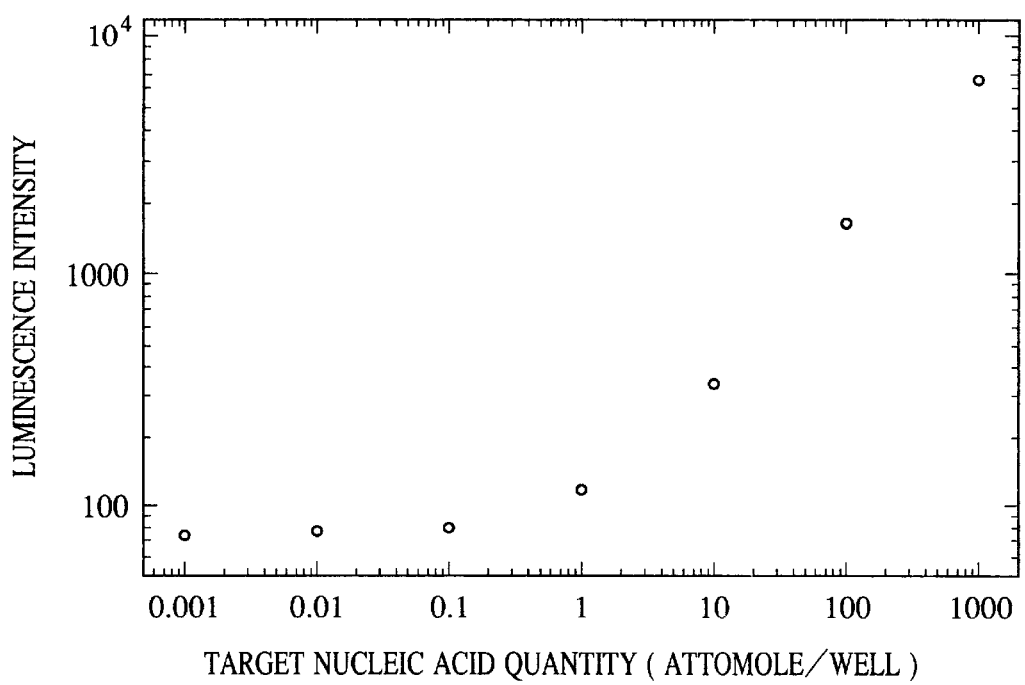

Each well of a microplate subjected to the above-described operation (1) including hybridization and washing was further washed with 1 ml of dimethyl phthalate, then filled with 1 ml of the solution ii) and left standing at room temperature for 5 min. to intercalate the chemiluminescent compound into the resulting double-stranded nucleic acid, and washed with 1 ml of dimethyl phthalate 3 times. After the removal of the dimethyl phthalate, each 600 μl of the solution i) and each 400 μl of the solution iii) were added to each well and immediately mixed. Succeedingly, similar to Example 5, 10 sec. after the addition of the solutions i) and iii) the luminescence intensity was measured while being consistently stirred by a stirrer disposed in the measurement apparatus. The results are shown in FIG. 8. As is obvious from FIG. 8, the detection sensitivity was approximately 1.0 attomole.

For comparison, a luminescence measurement was carried out in a manner similar to the above except that the washing treatment after the addition of the chemiluminescent compound solution ii) to the wells was omitted. Satisfactory measurement results could not, however, be obtained since the background in the measurement was excessively raised.

EXAMPLE 10
Detection of Double-Stranded DNA Using 4-Methyl-2,6-bis (4-N,N-dimethylaminophenyl)pyrylium Iodide (1) Hybridization Hybridization and other treatments were performed similar to operation (1) of Example 8 above, except that the 2-time-repeated washing treatment using a TE buffered solution after the washing treatment using the above-specified washing solution was carried out using a 10 mM phosphate buffered solution (pH 6.0).

(2) Detection of Luminescence

The following reagents were used for detection of luminescence.

i) 0.2 M $H_2O_2$ Solution

Two milliliters of a 30% by weight $H_2O_2$ aqueous solution was added to a mixture comprising 5 ml of dimethylsulfoxide (DMSO) and 93 ml of a 10 mM phosphate buffered solution (pH 6.0), and then well mixed to prepare a 0.2 M $H_2O_2$ solution.

ii) Chemiluminescent Compound Solution

To 1 ml of DMSO, 4.5 mg of 4-methyl-2,6-bis(4-N,N-dimethylaminophenyl) pyrylium iodide was dissolved, and the resulting mixture was then added to and mixed with 9 ml of a 10 mM phosphate buffered solution (pH 6.0). The resulting mixture was 400-fold-diluted with a 10 mM phosphate buffered solution (pH 6.0) containing 5% by weight of DMSO to prepare a 0.25 $\mu$M chemiluminescent compound solution.

iii) 2.5 mM DNPO Solution

In a mixture comprising 4 ml of DMSO and 36 ml of a 10 mM phosphate buffered solution (pH 6.0), 42 mg of DNPO was dissolved to prepare the object solution.

Figure 9:
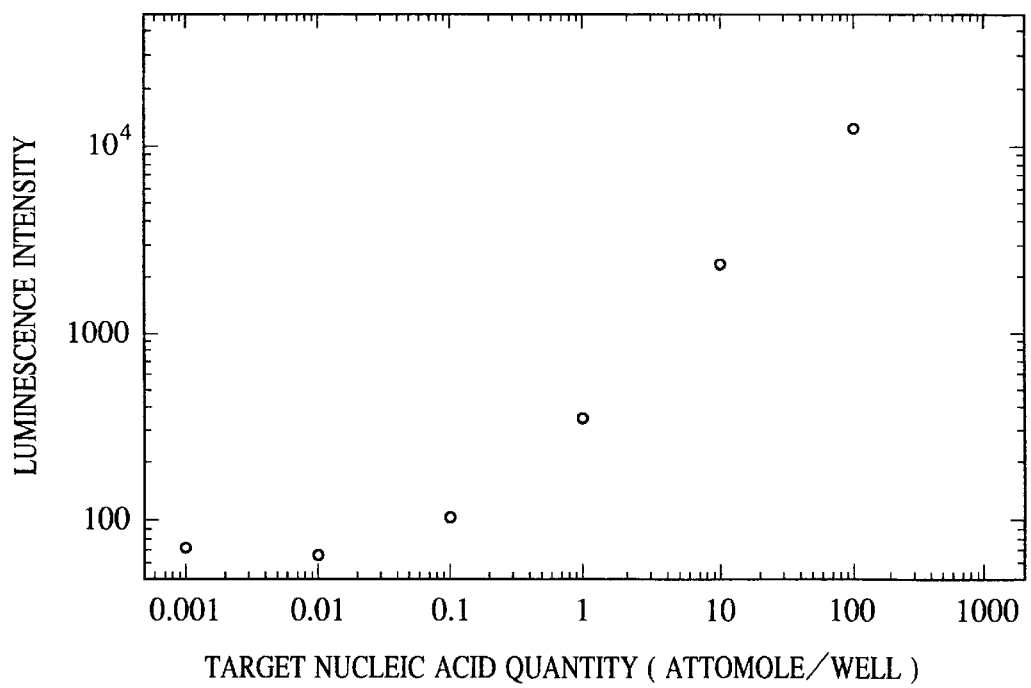

Each 400 $\mu$l of the solution ii) was added to each well of a microplate subjected to the hybridization and the washing treatments as described in the above paragraph (1), and left standing at room temperature for 5 min. to intercalate the chemiluminescent compound into the resulting double-stranded nucleic acids. After this, each 200 $\mu$l of the solution i) and each 400 $\mu$l of the solution iii) were added to each well and immediately mixed. Succeedingly, similar to Example 5, 10 sec. after the addition of the solutions i) and iii) the luminescence intensity was measured while being consistently stirred by a stirrer disposed in the measurement apparatus. The results are shown in FIG. 9. As is obvious from FIG. 9, the detection sensitivity was approximately 0.1 attomole.

EXAMPLE 11
Detection of mRNA Using 4-Methyl-2,6-bis(4-N,N-dimethylaminophenyl) pyrylium Iodide (1) Hybridization A probe nucleic acid having a base sequence complementary to a part of the MRNA base sequence of human $\beta_2$ adrenergic receptor and having an amino group at the 5' end was synthesized using a DNA synthesizer 381A manufactured by ABI Co., Ltd, and 5'-Aminomodifier C6 manufactured by Grain Research Co., Ltd. Incidentally, purification was performed by high performance liquid chromatography (HPLC) according to an ordinary method. The base sequence of thus-synthesized probe nucleic acid is as follows.

5'-$NH_2$-ATGCTGGCCGTGACGCACAGCA-3'      SEQ ID NO. 3

The above probe nucleic acid was dispensed to each well of a microplate (MS-3796F, manufactured by Sumitomo Bakelite Co., Ltd.), and immobilized on the microplate by using 1-ethyl-3-(3-dimethylaminopropyl) carbodiimide hydrochloride (EDC) and N-hydroxysulfosuccinimide (Sulfo-NHS), and forming a covalent bond between amino group of the probe nucleic acid and carboxyl group on the surface of the microplate.

Meanwhile, according to an ordinary method, a human $\beta_2$ adrenergic receptor mRNA was synthesized from a human $\beta_2$ adrenergic receptor cDNA using $T_7$ RNA polymerase, and purified after a DNase treatment.

The microplate wells on which the aforementioned probe nucleic acid was immobilized was treated with each 250 $\mu$l of a 10 mM phosphate buffered solution (pH 7.0) at 45° C. for 1 hour, and the treatment solution was then removed together with DNase. Next, each 50 $\mu$l of 10 mM phosphate buffered solutions (pH 6.0) respectively containing 0.001, 0.01, 0.1, 1.0, 10, 100 and 1000 attomoles of the human $\beta_2$ adrenergic receptor mRNA were added to the wells one by one, heated at 70° C. for 10 min, and then left standing to be cooled to the room temperature, thus hybridizing the probe nucleic acid and the target nucleic acid. After hybridization, the mixture in each well was removed, and the resulting microplate was subjected to the succeeding operation (2) described below.

(2) Detection of Luminescence

The following reagents were used for detection of luminescence.

i) 0.2 M $H_2O_2$ Solution

Two milliliters of a 30% by weight $H_2O_2$ aqueous solution was added to a mixture comprising 5 ml of dimethylsulfoxide (DMSO) and 93 ml of a 10 mM phosphate buffered solution (pH 6.0), and then well mixed to prepare a 0.2 M $H_2O_2$ solution.

ii) Chemiluminescent Compound Solution

To 1 ml of DMSO, 4.5 mg of 4-methyl-2,6-bis(4-N,N-dimethylaminophenyl) pyrylium iodide was dissolved, and the resulting mixture was then added to and mixed with 9 ml of a 10 mM phosphate buffered solution (pH 6.0). The resulting mixture was 400-fold-diluted with a 10 mM phosphate buffered solution (pH 6.0) containing 5% by weight of DMSO to prepare a 0.25 $\mu$M chemiluminescent compound solution.

iii) 2.5 mM DNPO Solution

In a mixture comprising 4 ml of DMSO and 36 ml of a 10 mM phosphate buffered solution (pH 6.0), 42 mg of DNPO was dissolved to prepare the object solution.

Figure 10:
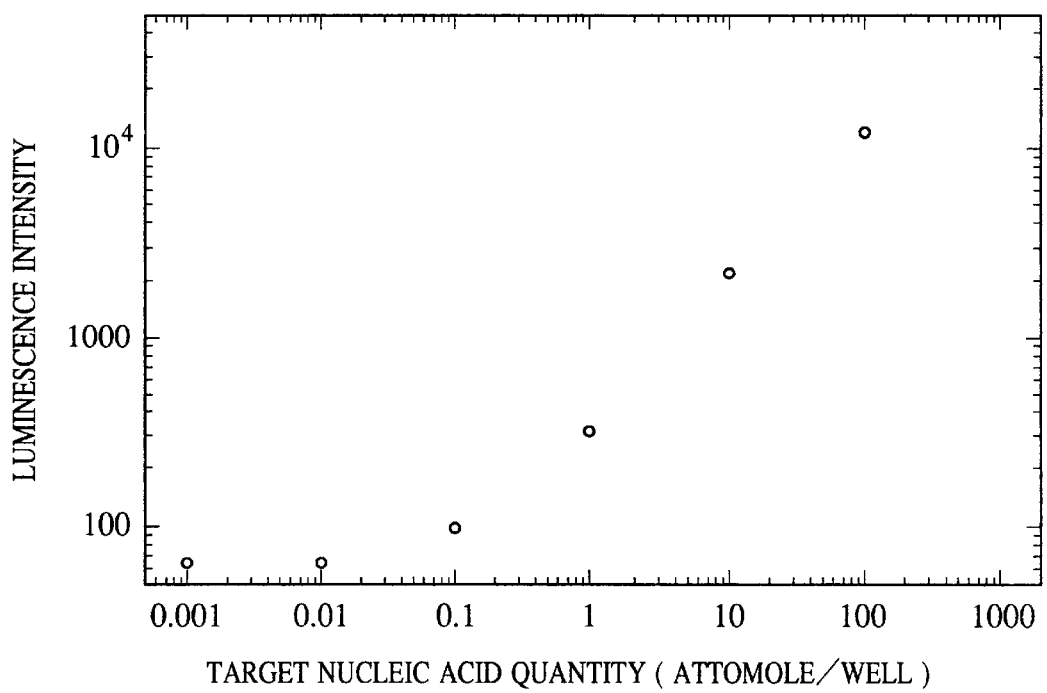

Each 100 $\mu$l of the solution ii) was added to each well of the microplate subjected to the hybridization operation (1), and after being well-mixed, left standing at room temperature for 5 min. to intercalate the chemiluminescent compound into the resulting double-stranded nucleic acids. After this, the mixture in each well was removed, and each 50 $\mu$l of the solution i) and each 100 $\mu$l of the solution iii) were added to each well and immediately mixed. Succeedingly, similar to Example 5, the luminescence intensity 10 sec. after the addition of the solutions i) and iii) was measured while being consistently stirred by a stirrer disposed in the measurement apparatus. The results are shown in FIG. 10. As is obvious from FIG. 10, the detection sensitivity was approximately 0.1 attomole.

EXAMPLE 12
Quantification of mRNA in Unknown Sample Using 4-Methyl-2,6-bis(4-N,N-dimethylaminophenyl) pyrylium Iodide (1) Drawing of Calibration Curve Similar to Example 11, a microplate on which a probe nucleic acid was immobilized was prepared, a human $\beta_2$ adrenergic receptor MRNA was then added to each well of the microplate, hybridization and detection of luminescence were carried out, and a calibration curve was obtained from the results of the detection.

(2) Preparation of Sample and Quantification of mRNA in Sample

Human HL 60 promyelocytic leukemia cells were cultured and collected by centrifugation, and washed with PBS (pH 7.4). The cells were then divided into suspensions having concentrations of $1 \times 10^3$, $1 \times 10^4$, $1 \times 10^5$, $1 \times 10^6$ and $1 \times 10^7$ cells/ml, respectively, repeatedly made to pass through a plastic syringe equipped with a 21-gauge needle, and then incubated in PBS at 45° C. for 1 hour. From each sample suspension, the total RNA was extracted and purified using a total RNA separator kit manufactured by CloneTech Co., Ltd. Thus-obtained each total RNA sample was dissolved in PBS, reacted with a probe nucleic acid immobilized in each well of a microplate, and then subjected to detection of luminescence in a manner similar to Example 11. The human $\beta_2$ adrenergic receptor MRNA in each sample was quantified referring the observed luminescence-intensity values to the previously drawn calibration curve. As a result, $1 \times 10^{-21}$ moles/cell (1 fg/cell) of the target nucleic acid could be detected in the sample derived from the suspension having a concentration of $1 \times 10^4$ cells/ml. This means that the weight of $1 \times 10^{-21}$ moles of the target nucleic acid is 1 fg (femtogram).

EXAMPLE 13

Detection of Target Nucleic Acid with Extension of Double-Stranded Portion (1) Immobilization of Probe Nucleic Acid The sequence of M13 Primer M4 d SEQ ID No. 4 (GTTTTCCCAGTCACGAC) is selected, and modified at the 5' end with an amino group based on the method in Example 11. The thus-synthesized probe DNA was immobilized to a microplate by covalent binding.

(2) Hybridization and Extension of Double-Stranded Portion

Solutions respectively containing $0.01 \times 10^{-21}$, $0.1 \times 10^{-21}$, $1.0 \times 10^{-21}$, $10 \times 10^{-21}$ and $100 \times 10^{-21}$ moles of a target nucleic acid, i.e. a single-stranded DNA M13mp18, were added to the wells of the microplate except a well for a blank test, respectively, and hybridization was carried out in the same procedure as that in Example 7. After the hybridization, the double-stranded portions were extended using a DNA polymerase, Taq DNA Polymerase manufactured by Toyobo Co., Ltd., while the single-stranded portions respectively adjacent the double-stranded portions were made to serve as templates. The conditions for extension were based on the protocol recommended by the manufacturer, and the reaction time period was 1 hour.

(3) Detection of Luminescence

Figure 11:
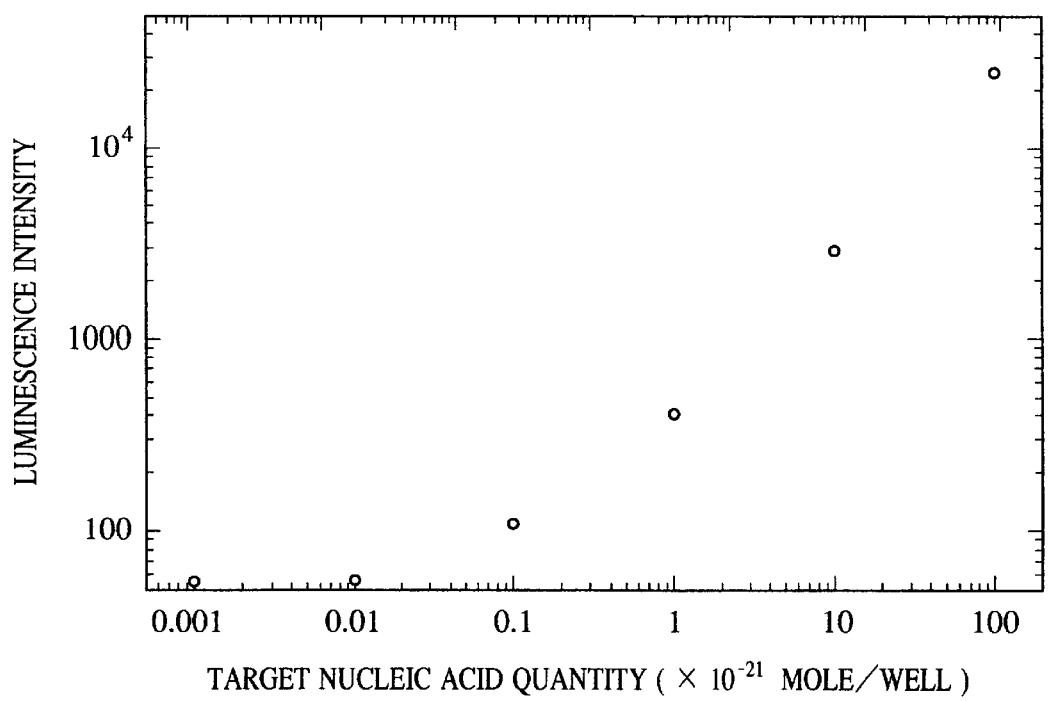

The wells subjected to the extension reaction were washed with a 10 mM phosphate buffered solution (pH 6.0) to remove the DNA polymerase and the nucleotide monomers, and detection of luminescence was carried out using 4-methyl-2,6-bis (4-N,N-dimethylaminophenyl) pyrylium iodide in a manner similar to Example 11. The results are shown in FIG. 11. As is obvious from FIG. 11, the detection sensitivity was approximately 0.1 to $1.0 \times 10^{-21}$ mole. Accordingly, by the extension of the double-stranded portion, detection sensitivity was improved by two to three orders of magnitude as compared to Example 7.

EXAMPLE 14

Detection of Target Nucleic Acid With Extension of Double-Stranded Portion (1) Immobilization of Probe Nucleic Acid In the manner similar to operation (1) of Example 11, a probe nucleic acid for detection of the human $\beta_2$ adrenergic receptor mRNA was immobilized to a microplate.

(2) Hybridization

In the manner similar to the operation (2) of Example 11, solutions containing the human $\beta_2$ adrenergic receptor mRNA at predetermined concentrations were added to the wells of the microplate, respectively, and hybridization was carried out.

(3) Extension of Double-Stranded Portion

After the completion of the above hybridization (2), the wells of the microplate were washed, and a nucleic-acid-extension reaction was performed according to an ordinary method using 1st-Strand cDNA Synthesis Kit manufactured by CloneTech Co., Ltd., wherein the probe nucleic acid was made to serve as a primer, and the single-stranded portion of the target nucleic acid was made to serve as a template.

(4) Detection of Luminescence

Figure 12:
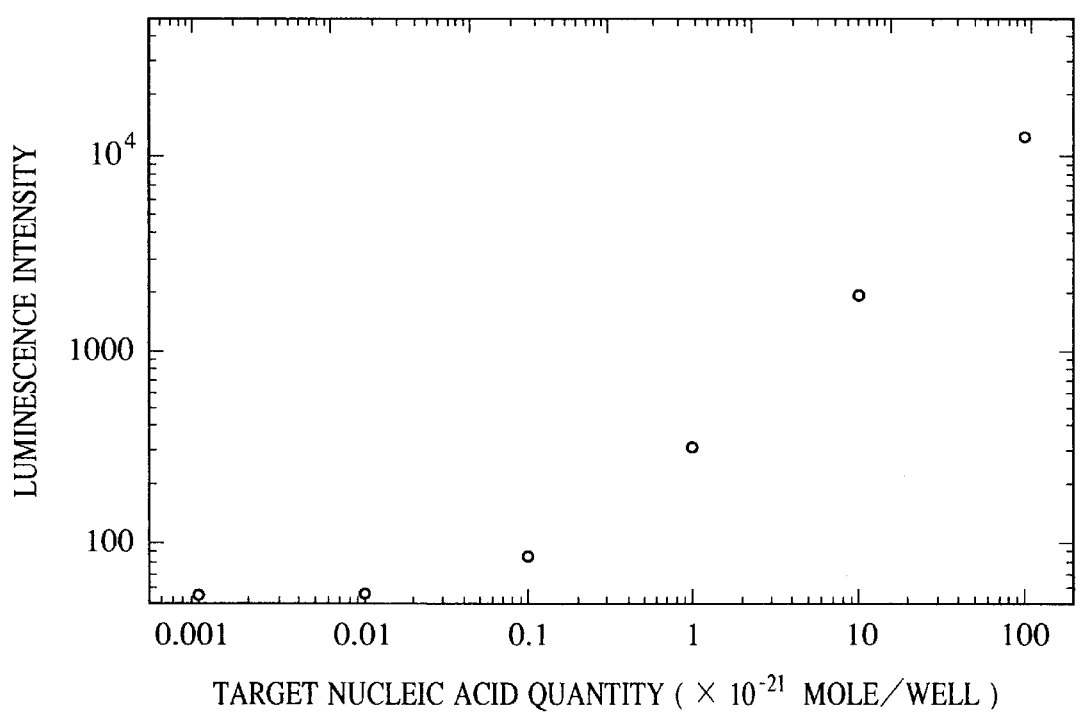

The wells subjected to the extension reaction were washed with a 10 mM phosphate buffered solution (pH 6.0) to remove the reverse transcriptase and the nucleotide monomers, and detection of luminescence was carried out using 4-methyl-2,6-bis(4-N,N-dimethylaminophenyl) pyrylium iodide in a manner similar to Example 11. The results are shown in FIG. 12. As is obvious from FIG. 12, the detection sensitivity was approximately 0.1 to $1.0 \times 10^{-21}$ mole. Accordingly, by the extension of the double-stranded portion, detection sensitivity was improved by two to three orders of magnitude as compared to Example 11.

EXAMPLE 15

Synthesis of 2-Methyl-4,6-bis(4-N,N-dimethylaminophenyl) pyrylium Iodide 100 ml of acetic anhydride and 30 ml of concentrated sulfuric acid were mixed while cooling, and the mixture was then heated at 80° C. for 3 hours in a water bath. To the mixture, 20 ml of acetic anhydride and 30 ml of p-dimethylaminoacetophenone were added at room temperature, and the resulting mixture then heated to 45° C. and reacted for 24 hours while stirring. To this reaction mixture, an equal volume of ethanol was added. After cooling, a potassium iodide solution was further added to precipitate crude crystals. The crude crystals were then recovered by filtration, and recrystallized in a mixture system of ethanol/ether (1:4 by volume per volume) to obtain green crystals of 2-methyl-4,6-bis(4-N,N-dimethylaminophenyl) pyrylium iodide (Compound 1 in Table 1, wherein Y is I).

Analysis Results of the Obtained Compound 1 (Y= I)

Melting Point: 254 to 257° C.

Maximal Absorbance in UV or Visible Region [$\lambda_{max}$ (CH$_3$CN, $\epsilon \times 10^{-4}$)]: 444 nm (2.43), 550 nm (8.24)

NMR($^1$H, DMSO) δ ppm: 8.3737(1H, s), 8.2729(1H, d, J×9.0 Hz), 8.1795(1H, d, J×9.0 Hz), 7.8864(1H, s), 6.9117 (4H, t, $J_{AB}=J_{BC}$=9.77 Hz), 3.1829(6H, s), 3.1340(6H, s), 2.6809(3H, s)

FAB mass (m/z): 333

IR (KBr, V cm-1): 1645, 1610(sh), 1580(s), 1490(s), 1270, 1200, 1160

Measurement of Luminescent Intensity

<Preparation of Reagent and Sample Solutions> i) 0.2 M H$_2$O$_2$ Solution

Two milliliters of a 30% by weight $H_2O_2$ aqueous solution was added to a mixture comprising 20 ml of t-butyl alcohol and 80 ml of dimethyl phthalate, and then well mixed.

ii) Chemiluminescent Compound Solution

The above-prepared 2-methyl-4,6-bis(4-N,N-dimethylaminophenyl) pyrylium iodide was dissolved in dimethyl phthalate such that the absorbance of the resulting solution was 0.5.

iii) 2.5 mM DNPO Solution

In 40 ml of dimethyl phthalate, 42 mg of DNPO was dissolved.

<Measurement Procedure>

Each 1 ml of the above solutions i) and ii) were placed into a quartz cell for fluorescence measurement having a size of 1 cm×1 cm (optical path length×optical path width), and well mixed. After this, the solution iii) was added and immediately mixed, and the luminescence spectrum was examined using an optical multidetection system IMUC-7000 (Otsuka Electronic Industries, Co., Ltd.). The wavelength where the chemiluminescent compound (Compound "a") exhibited the maximal luminescent intensity, and the relative luminescence intensity of Compound "a" are shown in Table 3, wherein the integral value of the maximal luminescence intensity is normalized with concentration, and the luminescence intensity of rhodamine B is assumed as 100.

EXAMPLE 16

Luminescence Intensities of Various Chemiluminescent Compounds

The relative luminescence intensities of various chemiluminescent compounds, and the wavelengths where the compounds exhibit the maximal luminescence intensities were measured in the same manner as Example 15, except that Compounds "b" to "r" and rhodamine B were respectively used instead of Compound "a". The results are shown in Table 3.

TABLE 3

| Compound ID | General Formula | X | Y | Luminescence wavelength (nm) | Relative Luminescence Intensity (integral value) |
|---|---|---|---|---|---|
| a | [7] | O | I | 645 | 600 |
| b | [7] | S | I | 700 | 150 |
| c | [8] | O | ClO$_4$ | 435 | 775 |
| d | [8] | S | ClO$_4$ | 465 | 185 |
| e | [9] | O | I | 670 | 230 |
| f | [9] | S | I | 720 | 85 |
| g | [10] | O | ClO$_4$ | 440 | 295 |
| h | [10] | S | ClO$_4$ | 500 | 100 |
| i | [11] | O | I | 630 | 60 |
| j | [11] | S | I | 690 | 30 |
| k | [12] | O | I | 690 | 85 |
| l | [12] | S | I | 745 | 30 |
| m | [13] | O | I | 720 | 135 |
| n | [13] | S | I | 770 | 50 |
| o | [14] | O | I | 700 | 185 |
| p | [14] | S | I | 760 | 70 |
| q | [15] | O | ClO$_4$ | 450 | 250 |
| r | [15] | S | ClO$_4$ | 470 | 85 |
| Rhodamine B | | | | 585 | 100 |

Table 4 shows the relative luminescence intensities of various fluorescent compounds measured using a typical oxalic ester, bisdinitrophenyl oxalate (DNPO), and hydrogen peroxide as luminescent-inducing reagents, wherein the relative luminescence intensities are shown as the values when the intensity values of rhodamine B is assumed as 100 and based on the description of a publication, "Seibutsuhakkou to Kagakuhakkou, Kiso to Jikken (Bioluminescence and Chemiluminescence, Fundament and Experiments)" (pp. 77–108, published on Jan. 10, 1989 by Hirokawa Publishing Co.), and the luminescence wavelengths were measured by the Inventors.

TABLE 4

| Fluorescent Compound | Luminescence Wavelength (nm) | Relative Luminescence Intensity |
|---|---|---|
| Perylene | 470 | 500 |
| Rubrene | — | 170 |
| Rhodamine B | 585 | 100 |
| DSN-Alanine | 510 | 60 |
| 3-Methylcholanthrene | — | 55 |
| Rose Bengal | — | 35 |
| Benzo[α]pyrene | 450 | 15 |
| NBD-Proline | 530 | 3.2 |
| 9,10-Dibromoanthracene | 440 | 1.2 |
| Riboflavin | 535 | 0.18 |
| Fluorescein | 510 | 0.12 |
| SBD-Mercaptoethanol | — | 0.06 |
| Umbelliferone | — | 0.06 |
| α-Tocopherol | 440 | >0.05 |
| NADH | — | >0.05 |
| Pyridoxine Hydrochloride | — | >0.05 |

As is obvious from Table 4, the fluorescent compound exhibiting higher fluorescence yields, such as fluorescein, does not necessarily exhibit higher luminescence intensities.

Comparing the data in Table 3 to that in Table 4, the luminescent compounds according to the present invention are found to exhibit luminescence intensities extremely higher than, or equal to or higher than, the conventional luminescent compounds. Further, since such luminescent compounds exhibiting higher luminescence intensities belong to the group of pyrylium or thiapyrylium, they exhibit similarity in the chemical characteristics such as solubility, and therefore, a plurality of such luminescent compounds can be readily used in one system. Moreover, in addition to higher luminescence intensities, since the deviation in luminescence intensity falls within one order of magnitude, a plurality of such luminescent compounds can be used without any special modification of the measurement apparatus. Furthermore, as is obvious from Table 3, since the luminescent compounds according to the present invention exhibit luminescence in wavelength regions from near-ultraviolet to near-infrared, they are markedly advantageous for multi-parameter analysis in one system.

EXAMPLE 17

Quantification of Hydrogen Peroxide Using Compound "c", 2-Methyl-4,6-diphenylpyrylium Perchlorate, Shown in Table 3

(1) Preparation of Reagent and Sample Solutions i) $H_2O_2$ Solutions

Appropriate amounts of $H_2O_2$ solutions (prepared by appropriately diluting a 30% by weight $H_2O_2$ aqueous solution) were respectively added to mixtures each comprising t-butyl alcohol and dimethyl phthalate, and were well mixed to prepare $H_2O_2$ solutions having concentrations of 0.5, 1.0, 5.0, 50, 500 and 5000 fM, respectively.

ii) Chemiluminescent Compound Solution

Compound "c" shown in Table 3 was dissolved in dimethyl phthalate to prepare a 50 μM solution.

iii) 2.5 mM DNPO Solution

In 40 ml of dimethyl phthalate, 42 mg of DNPO was dissolved.

(2) Measurement of Luminescence Intensity In a polystyrene cell for Luminometer 1251 manufactured by BioOrbit Co., Ltd., 200 μl of the above-prepared solution i) and 400

μl of the solution ii) were placed, and the cell was put in a sample chamber of the luminometer. After this, 400 μl of the solution iii) was further added using an adjunct dispenser while being consistently stirred the mixture by a stirrer disposed in the luminometer. Luminescence intensity was measured and the integral value of luminescence intensity from 5 to 15 sec. after the start of the operation of the dispenser (including the time when the maximum luminescence intensity was exhibited) was obtained. The results are shown in FIG. 13 (for the sake of convenience, the blank value observed in the absence of hydrogen peroxide is plotted as the value when the concentration of hydrogen peroxide is 0.01 fM).

Figure 13:
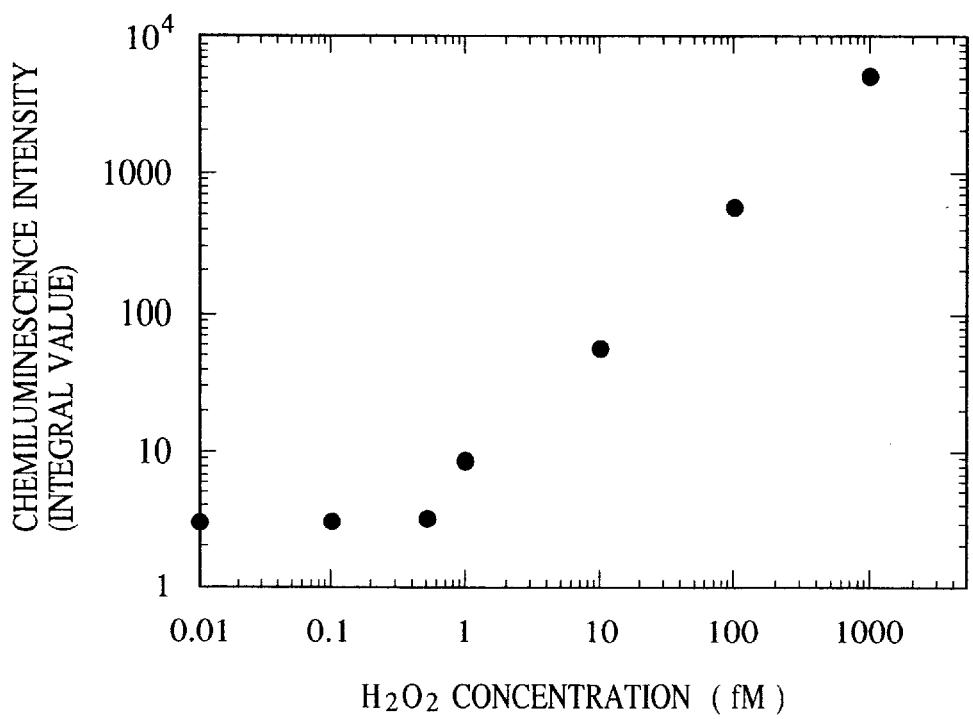
FIGS. 13, 14, and 15 show the results of quantification of hydrogen peroxide using Compounds "c", "a" and "p" listed in Table 3, respectively.

As is obvious from FIG. 13, the limit of Compound "c" in detection of hydrogen peroxide is approximately 1 fM.

EXAMPLE 18
Quantification of Hydrogen Peroxide Using Compound "a", 2-Methyl-4,6-bis(4-N,N-dimethylaminophenyl) pyrylium Iodide, Shown in Table 3

Quantification of hydrogen peroxide was carried out in the same manner as in Example 17 except that Compound "a" was used instead of Compound "c". The results are shown in FIG. 14 (for the sake of convenience, the blank value observed in the absence of hydrogen peroxide is plotted as the value when the concentration of hydrogen peroxide is 0.01 fM).

Figure 14:
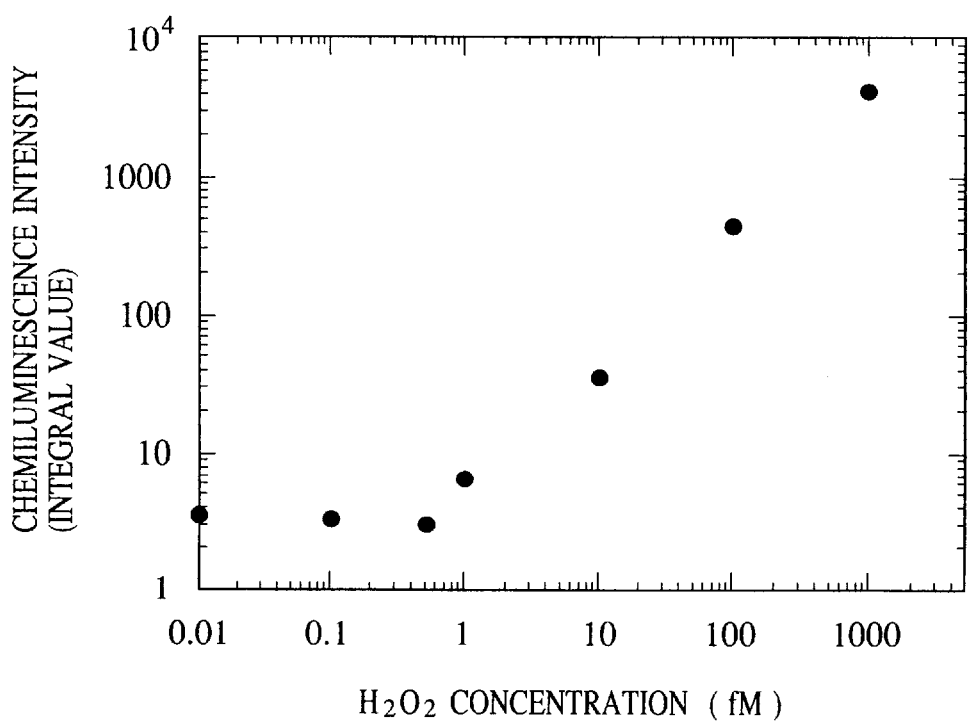

As is obvious from FIG. 14, the limit of Compound "a" in detection of hydrogen peroxide is approximately 1 fM, similar to Compound "c".

EXAMPLE 19
Quantification of Hydrogen Peroxide Using Compound "p", 2,4,6-Tris(4-N,N-dimethylaminophenyl) thiapyrylium Iodide, Shown in Table 3

Quantification of hydrogen peroxide was carried out in the same manner as in Example 17 except that Compound "p" was used instead of Compound "c". The results are shown in FIG. 15 (for the sake of convenience, the blank value observed in the absence of hydrogen peroxide is plotted as the value when the concentration of hydrogen peroxide is 0.01 fM).

Figure 15:
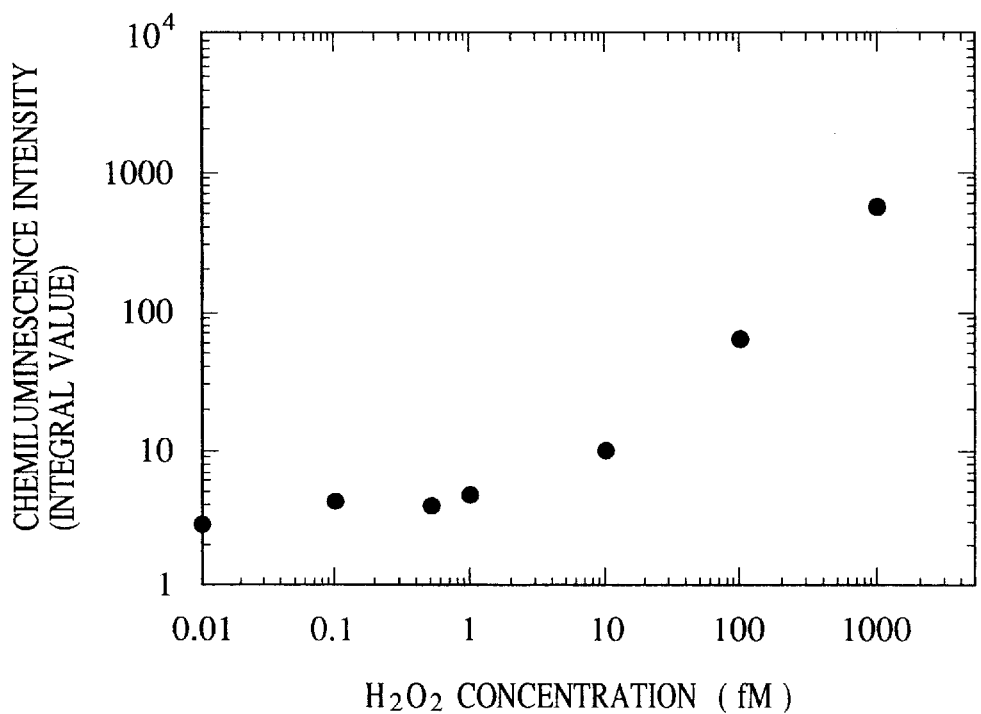

As is obvious from FIG. 15, the limit of Compound "p" in detection of hydrogen peroxide is approximately 10 fM.

Comparative Example 1
Quantification of Hydrogen Peroxide Using Rhodamine B

Quantification of hydrogen peroxide was carried out in the same manner as in Example 17 except that Rhodamine B was used instead of Compound "c". The results are shown in FIG. 16 (for the sake of convenience, the blank value observed in the absence of hydrogen peroxide is plotted as the value when the concentration of hydrogen peroxide is 0.01 fM).

Figure 16:
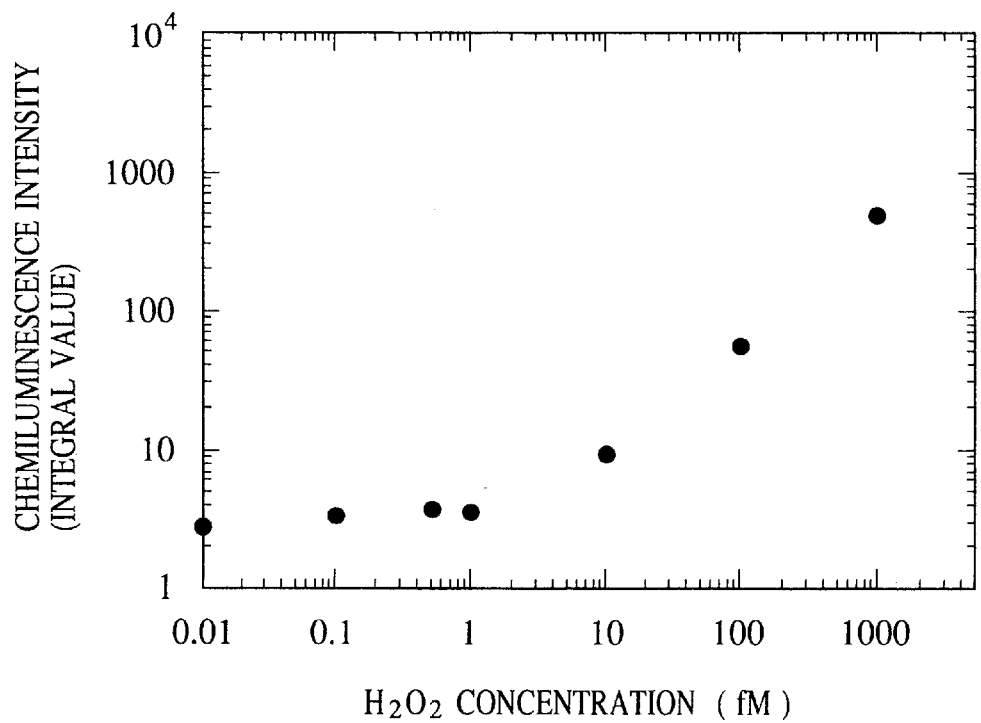
FIG. 16 shows the results of quantification of hydrogen peroxide using rhodamine B.

As is obvious from FIG. 16, the limit of Rhodamine B in detection of hydrogen peroxide is approximately 10 fM.

From the results of Examples 17 to 19 and Comparative Example 1, it can be understood that the pyrlium compounds according to the general formula [1] have sufficient detection sensitivities in wavelength regions from near-ultraviolet to near-infrared as compared to conventional luminescent compounds.

EXAMPLE 20
Chemiluminescence Characteristics

The chemiluminescence characteristics of the chemiluminescent compound No. 6 and No. 16 shown in Table 1 were examined under the same luminescence conditions as those in Example 15. The results are shown in Table 5, in which the relative luminescence intensity is expressed by the value when the value of rhodamine B is assumed as 100. As is obvious from the results, the compound No. 6 and No. 16 exhibit sufficient luminescence intensities even in a long-wavelength region.

TABLE 5

| Compound No. | X | Y | Luminescence Wavelength (nm) | Relative Luminescence Intensity (integral value) |
|---|---|---|---|---|
| 6 | S | I | 800 | 105 |
| 16 | S | $ClO_4$ | 825 | 65 |

As described above, according to the present invention, the target double-nucleic can be detected or quantified without a raised background at an extremely high sensitivity, such as a concentration level of 0.1 fM (in terms of base pair) or an absolute-quantity level of 0.1 attomoles (in terms of base pair).

Further, according to the present invention, since chemiluminescence is utilized for detecting the double-stranded nucleic acid, the problems inherent in fluorescence methods can be removed. Moreover, since the chemiluminescent compound is used after the step of forming the double-stranded nucleic acid, the probe nucleic acid can be prevented from being destabilized, which may occur in the case where the probe nucleic acid is labelled.

In the present invention, the detection of the double-stranded nucleic acid including the target nucleic acid is preferably carried out in a state where the chemiluminescent compound is associated with the double-stranded nucleic acid, or under a condition in which the chemiluminescent compound acquires chemiluminescent ability only when associated with double-stranded nucleic acids. According to such a manner, since the step of removing the chemiluminescent compound molecules not associated with the double-stranded nucleic acid from the reaction system becomes unnecessary, the detecting operation can be remarkably simplified, and a highly sensitive detection with an effectively lowered background can be achieved.

In addition, when the double-stranded portion of the hybrid which comprises the target nucleic acid and the probe nucleic acid and which is formed on the solid phase is extended by extension reaction, the portion for association with the chemiluminescent compound can also be extended. As a result, detection of the double-stranded nucleic acid can be further facilitated, and the detection sensitivity can be further enhanced.

Meanwhile, the luminescent compounds according to the present invention exhibit luminescence intensities extremely higher than, or equal to or higher than, the conventional luminescent compounds. Since such luminescent compounds belong to the compound group of pyrylium or thiapyrylium, they exhibit similarity in the chemical characteristics such as solubility, and therefore, a plurality of such luminescent compounds can be readily used in one system. Moreover, in addition to higher luminescence intensities, since the deviation in their luminescence intensities falls within one order of magnitude, a plurality of such luminescent compounds can be used without any special modification of the measurement apparatus. Furthermore, as shown in Tables 3 and 5, since the luminescent compounds according to the present invention exhibit luminescence in wavelength regions from near-ultraviolet to near-infrared, they are markedly advantageous for multi-parameter analysis in one system.

What is claimed is:

1. A process for detecting a target single-stranded nucleic acid having a first base sequence, said process comprising the steps of:
   (a) forming a double-stranded nucleic acid by hybridizing said target single-stranded nucleic acid with a probe nucleic acid having a second base sequence complementary to the first base sequence;
   (b) associating a chemiluminescent compound with the double-stranded nucleic acid;
   (c) exposing the chemiluminescent compound associated with said double-stranded nucleic acid to at least two luminescence-inducing compounds which generate energy which excites the associated chemiluminescent compound into luminescence; and
   (d) detecting the luminescence from the chemiluminescent compound excited in step (c), wherein said step (c) is conducted such that (i) only the associated chemiluminescent compound emits luminescence, and (ii) the detected luminescence is indicative of the target single-stranded nucleic acid and wherein said chemiluminescent compound is a compound represented by the following formula (7):

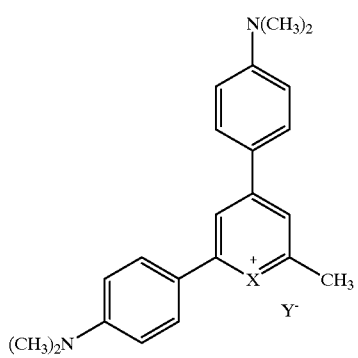

(7)

wherein X is O, S, Se, or Te, and Y– is an anion.

2. A process for detecting a target single-stranded nucleic acid having a first base sequence, comprising the steps of:
   (a) associating a chemiluminescent compound with a double-stranded nucleic acid formed between the target single-stranded nucleic acid and a single-stranded nucleic acid having a second base sequence which is complementary to the first base sequence;
   (b) exposing the chemiluminescent compound associated with the double-stranded nucleic acid to at least two luminescence-inducing compounds which generate energy which excites the associated chemiluminescent compound into luminescence; and
   (c) detecting the luminescence from said excited chemiluminescent compound, wherein the step (b) is conducted such that (i) only the associated chemiluminescent compound emits luminescence and (ii) the detected luminescence is indicative of the target single-stranded nucleic acid, and wherein said chemiluminescent compound is a compound represented by the following formula (7):

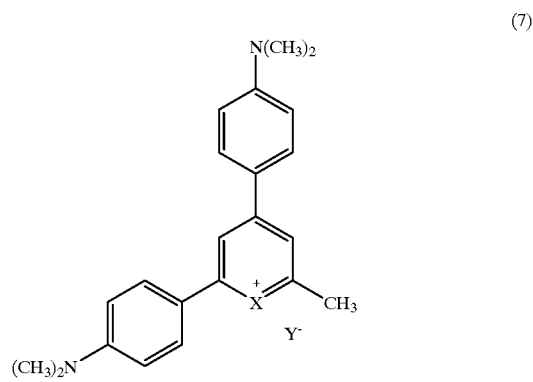

(7)

wherein X is O, S, Se, or Te, and Y– is an anion.

3. A process according to claim 1 or 2, wherein the luminescence-inducing compounds include an oxalic ester and a peroxide compound.

4. The process according to claim 3, wherein the oxalic ester is selected from the group consisting of oxalates and oxamides.

5. The process according to claim 4, wherein the oxalates include compounds represented by the following formula (16)–(24):

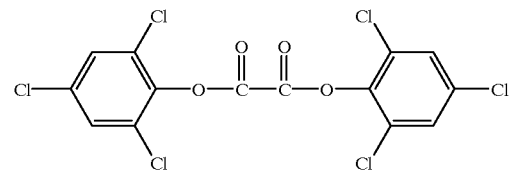

(16)

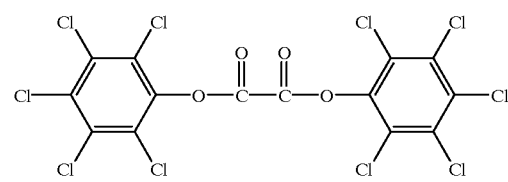

(17)

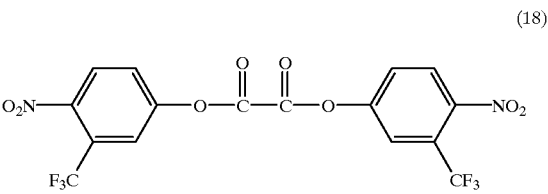

(18)

-continued

(19)
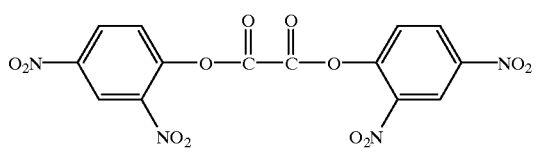

(20)
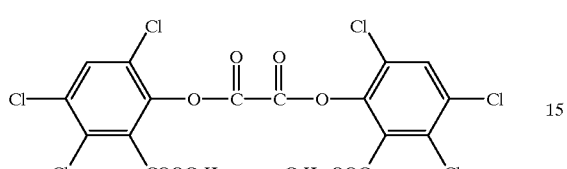

(21)
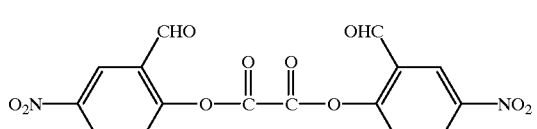

(22)
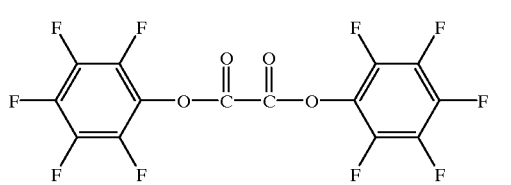

(23)
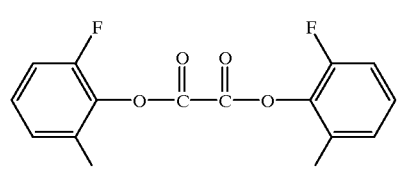

(24)
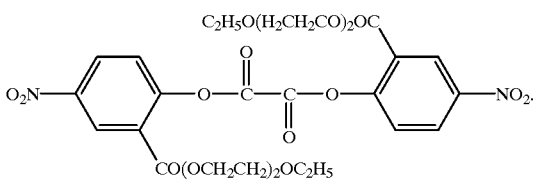

6. The process according to claim 4, wherein the oxamides include compounds represented by the following formulae (25)–(30):

(25)
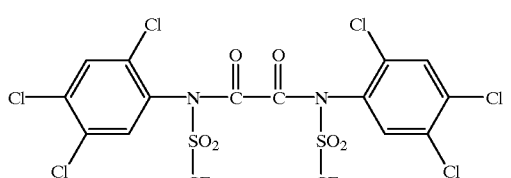

-continued

(26)
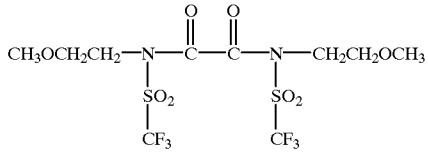

(27)
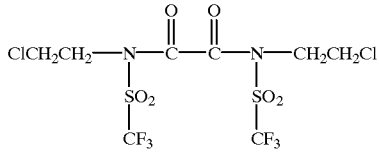

(28)
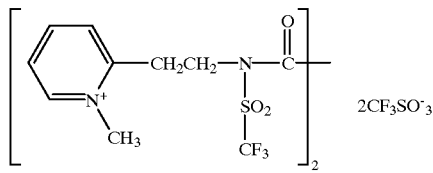

(29)
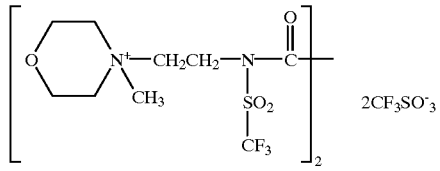

(30)
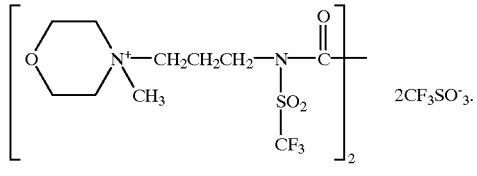

7. The process according to claim 1 or 2, wherein the exposing step is conducted in an aqueous medium.

8. The process according to claim 3, wherein the peroxide compound is hydrogen peroxide.

9. A process for detecting a target single-stranded nucleic acid having a first base sequence, said process comprising the steps of:
  (a) forming a double-stranded nucleic acid by hybridizing said target single-stranded nucleic acid with a probe nucleic acid having a second base sequence complementary to the first base sequence;
  (b) associating a chemiluminescent compound with the double-stranded nucleic acid;
  (c) exposing the chemiluminescent compound associated with the double-stranded nucleic acid to (i) an oxalic ester and (ii) a peroxide compound, the oxalic ester and the peroxide compound reacting with each other to generate energy which excites the associated chemiluminescent compound into luminescence; and
  (d) detecting the luminescence from said chemiluminescent compound associated with said double stranded nucleic acid, wherein the step (c) is conducted such that (i) only the associated chemluminescent compound emits luminescence, and (ii) the detected luminescence is indicative of the target single-stranded nucleic acid and wherein said chemiluminescent compound is a compound represented by the following formula (7):

(7)

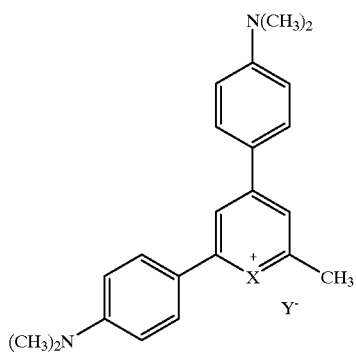

wherein X is O, S, Se, or Te, and Y– is an anion.

10. A process for detecting a target single-stranded nucleic acid having a first base sequence, comprising the steps of:

(a) associating a chemilumlinescent compound with a double-stranded nucleic acid formed between the target single-stranded nucleic acid and a single-stranded nucleic acid having a second base sequence complementary to the first base sequence;

(b) exposing the chemiluminescent compound associated with the double-stranded nucleic acid to (i) an oxalic ester and (ii) a peroxide compound, the oxalic ester and the peroxide compound reacting with each other to generate energy which excites the associated chemiluminescent compound into luminescence; and (c) detecting the luminescence from said chemiluminescent compound associated with said double-stranded nucleic acid, wherein the step (b) is conducted such that (i) only the associated chemiluminescent compound emits chemiluminesce, and (ii) the detected luminescence is indicative of the target single-stranded nucleic acid and wherein said chemiluminescent compound is a compound represented by the following formula (7):

(7)

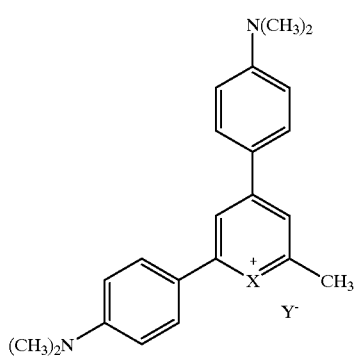

where X is O, S, Se, or Te, and Y– is an anion.

11. The process according to claim 9 or 10, wherein the oxalic ester is an oxalate.

12. The process according to claim 11, wherein oxalates include compounds represented by the following formulae (16)–(24):

(16)
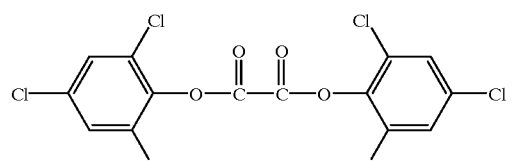

(17)
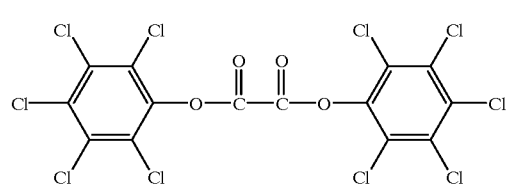

(18)
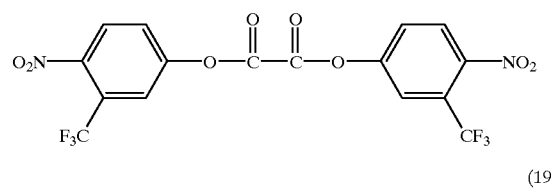

(19)
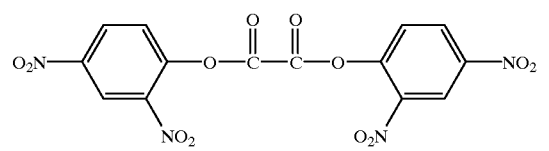

(20)
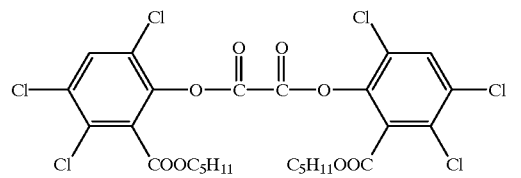

(21)
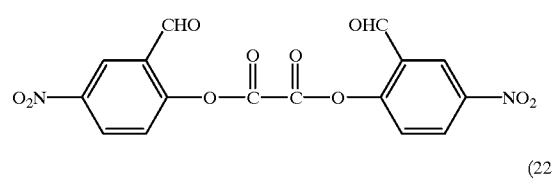

(22)
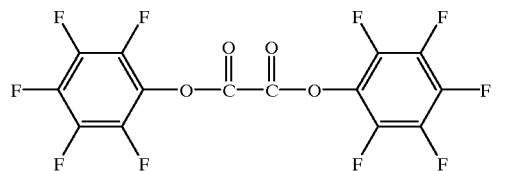

(23)

(24)

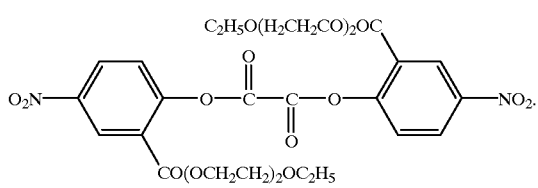

13. The process according to claim 9 or 10, wherein the oxalic ester is an oximide.

14. The process according to claim 13, wherein the oxamides include compounds represented by the following formulae (25)–(30):

(25)

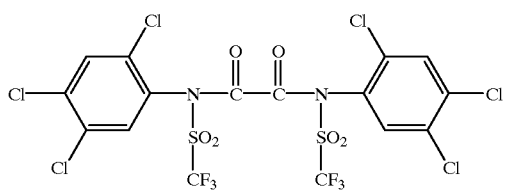

(26)

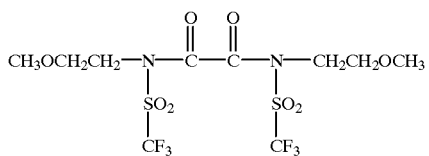

(27)

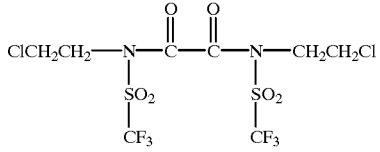

(28)

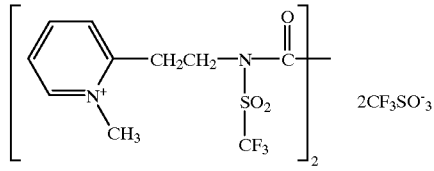

(29)

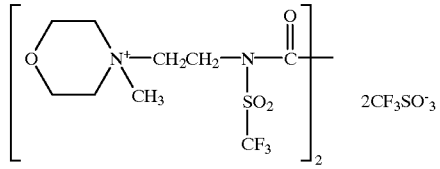

(30)

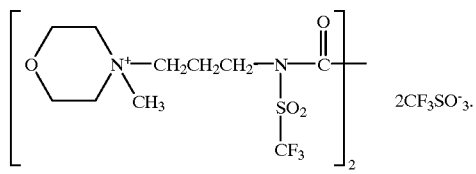

15. The process according to claim 1, 2, 9 or 10, wherein the exposing step is conducted in an aqueous medium.

16. The process according to claim 9 or 10, wherein the peroxide compound is hydrogen peroxide.

17. The process according to claim 15, wherein the aqueous medium is water.

18. The process according to claim 15, wherein the aqueous medium is an aqueous buffer solution.

19. The process according to claim 15, wherein said aqueous medium is a solution of water and an organic solvent miscible with water.

20. The process according to claim 19, wherein said organic solvent comprises at least one solvent selected from the group consisting of methanol, ethanol, acetonitrile, dimethylformamide, dimethylsulfoxide and isopropanol.

21. The process according to claim 19, wherein said organic solvent is present in amounts from 2 to 50% by volume based on the water.

22. The process according to claim 21, wherein said organic solvent is present in amounts from 5 to 20% by volume based on the water.

23. The process according to claim 15, wherein pH of said aqueous medium ranges from 5 to 8.

24. A process for determining the presence of a target single-stranded nucleic acid in a sample, comprising the steps of:

(a) providing a probe having a single-stranded nucleic acid whose base sequence is complementary to that of the target single-stranded nucleic acid;

(b) adding the probe to the sample, and then hybridizing the probe with the target single-stranded nucleic acid to form a double-stranded nucleic acid hybrid;

(c) adding to the sample resulting from the step (b) a chemiluminescent compound;

(d) associating the chemiluminescent compound with the double-stranded nucleic acid hybrid between the probe and the target single-stranded nucleic acid in the presence of two luminescence-inducing compounds, wherein the hybrid being formed in the step (b) if the sample contains the target single-stranded nucleic acid and wherein the luminescence-inducing compounds generating energy for exciting the associated chemiluminescent compound into luminescence; and (e) detecting, if present, luminescence from the chemiluminescent compound in an excited state, wherein the detected luminescence is indicative of the presence of the target single-stranded nucleic acid in the sample, wherein said step (d) is conducted such that only the chemiluminescent compound associated with the hybrid emits the luminescence, and wherein the chemiluminescent compound is represented by the following formula (7):

(7)

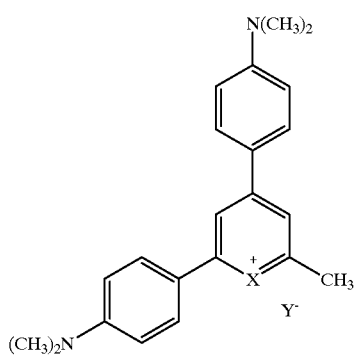

where X is O, S, Se, or Te, and Y− is an anion.

25. The process according to claim 24, wherein the luminescence-inducing compounds include an oxalic ester and a peroxide compound.

26. The process according to claim 25, wherein the oxalic ester is an oxalate.

27. The process according to claim 26, wherein the oxalate includes a compound represented by the following formulae (16)–(24):

(16)

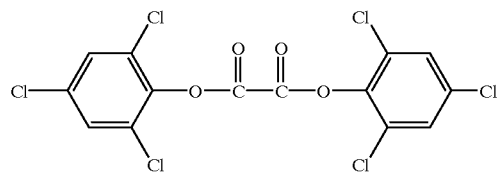

(17)

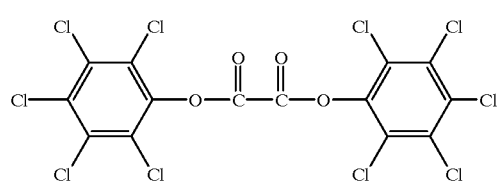

(18)

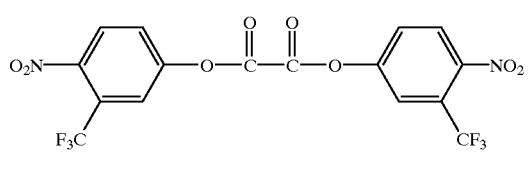

(19)

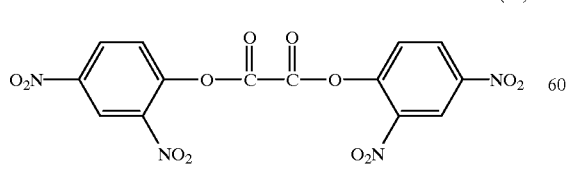

(20)

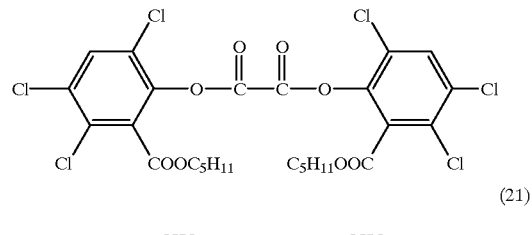

(21)

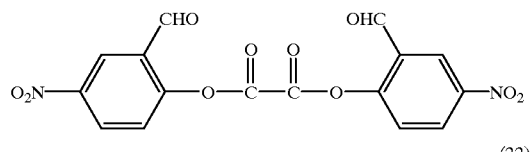

(22)

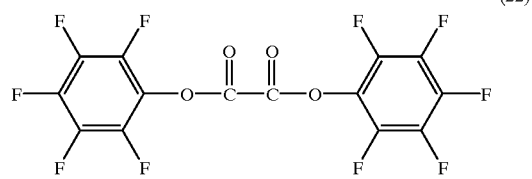

(23)

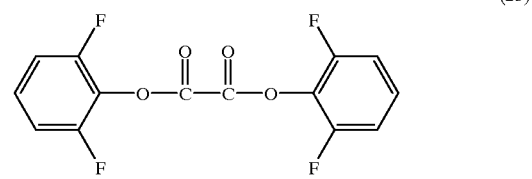

(24)

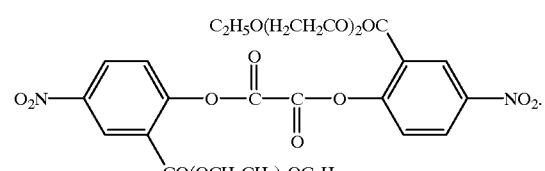

28. The process according to claim 25, wherein the oxalic ester is an oxamide.

29. The process according to claim 28, wherein the oxamide includes a compound represented by the following formula (25)–(30):

(25)

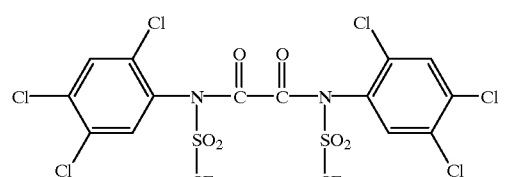

(26)

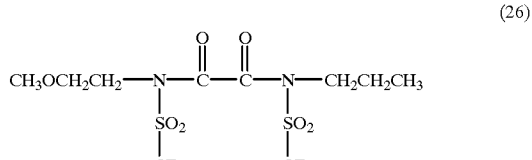

-continued

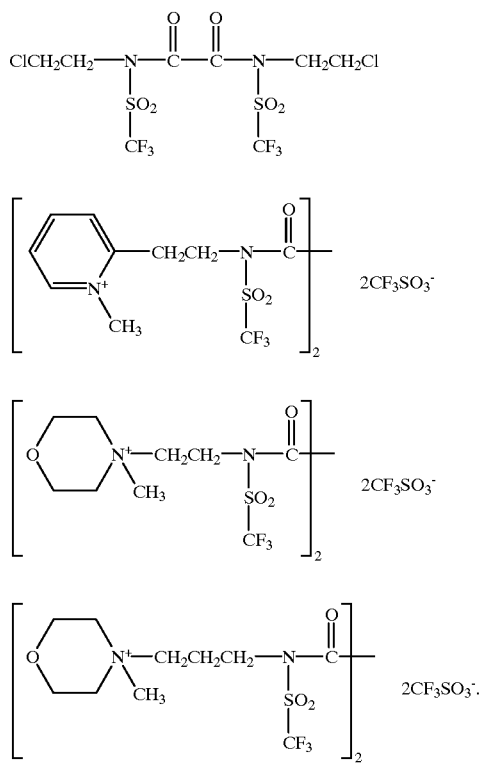

(27)

(28)

(29)

(30)

30. The process according to claim 24, wherein the step (d) is conducted in an aqueous medium.

31. The process according to claim 25, wherein the peroxide compound is a hydrogen peroxide.

32. The process according to claim 30, wherein the aqueous medium is water.

33. The process according to claim 30, wherein the aqueous medium is an aqueous buffer solution.

34. The process according to claim 30, wherein said aqueous medium is a solution of water and an organic solvent miscible with water.

35. The process according to claim 34, wherein said organic solvent comprises at least one solvent selected from the group consisting of methanol, ethanol, acetonitrile, dimethylformamide, dimethylsulfoxide and isopropanol.

36. The process according to claim 34, wherein said organic solvent is present in amounts from 2 to 50% by volume based on the water.

37. The process according to claim 36, wherein said organic solvent is present in amounts from 5 to 20% by volume based on the water.

38. The process according to claim 30, wherein pH of said aqueous medium ranges from 5 to 8.

* * * * *

UNITED STATES PATENT AND TRADEMARK OFFICE
CERTIFICATE OF CORRECTION

PATENT NO.     : 6,297,008 B1
DATED          : October 2, 2001
INVENTOR(S)    : Tadashi Okamoto et al.

It is certified that error appears in the above-identified patent and that said Letters Patent is hereby corrected as shown below:

Title page,
Item [56], References Cited, FOREIGN PATENT DOCUMENTS, "1275528" should read -- 1-275528 --.

Column 1,
Line 26, "ethidium.bromide" should read -- ethidium bromide --.

Column 3,
Line 59, "comprises" should read -- comprising --.

Column 4,
Line 3, "comprises" should read -- comprising --.

Column 7,
Line 8, "an" should read -- a --.

Column 13,
Compound 7, "$R_8$=n=0" should read -- $R_8$=Φ -- and group L should read -- n=0 --.

Column 17,
Compound 30, "$R_8$=Φ" should read -- $R_8$=L-A -- and "$R_{10}$=L-A" should read -- $R_{10}$=Φ --.

Column 21,
Compound 52, under group L "Φ—COOH" should be deleted and under group A insert -- —COOH --; and
Compound 53, under group L "Φ—COOH" should be deleted and under group A insert -- Φ—COOH --.

Column 25,
Line 42, "being emitted luminescence" should read -- luminescence being emitted --.

Column 30,
Line 41, "with in" should read -- with --; and
Line 48, "form" should read -- from --.

Column 41,
Line 21, "MRNA" should read -- mRNA --.

UNITED STATES PATENT AND TRADEMARK OFFICE
CERTIFICATE OF CORRECTION

PATENT NO.    : 6,297,008 B1
DATED         : October 2, 2001
INVENTOR(S)   : Tadashi Okamoto et al.

It is certified that error appears in the above-identified patent and that said Letters Patent is hereby corrected as shown below:

<u>Column 47/48 [SEQUENCE LISTING],</u>
ID. 2, "LENGTH: 22" should read -- LENGTH: 17 -- and --
    "ATGCTGGCCGTGACGCACAG CA 22" should read
    -- GTAAAACGAC GGCCAGT 17 --; and
ID. 3, "LENGTH: 17" should read -- LENGTH: 22 -- and
    "GTTTTCCCAGTCACGAC 17" should read
    -- ATGCTGGCCG TGACGCACAG CA 22 --.

Signed and Sealed this

Twenty-fifth Day of June, 2002

Attest:

JAMES E. ROGAN
*Attesting Officer*     *Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHETIC DNA"

(xi) SEQUENCE DESCRIPTION: SEQ ID NO: 1:

GTTTTCCCAG TCACGAC                                                              17

(2) INFORMATION FOR SEQ ID NO: 2:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHETIC DNA"

(xi) SEQUENCE DESCRIPTION: SEQ ID NO: 2:

ATGCTGGCCG TGACGCACAG CA                                                        22

(2) INFORMATION FOR SEQ ID NO: 3:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHETIC RNA"

(xi) SEQUENCE DESCRIPTION: SEQ ID NO: 3:

GTTTTCCCAG TCACGAC                                                              17

(2) INFORMATION FOR SEQ ID NO: 4

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHETIC DNA"

(xi) SEQUENCE DESCRIPTION: SEQ ID NO: 4:

GTTTTCCCAG TCACGAC                                                              17